US009662652B2

(12) United States Patent
Chen

(10) Patent No.: US 9,662,652 B2
(45) Date of Patent: *May 30, 2017

(54) SAMPLE PROCESSING DEVICE FOR PRETREATMENT AND THERMAL CYCLING

(75) Inventor: Shuqi Chen, Framingham, MA (US)

(73) Assignee: Chen & Chen, LLC, Framingham, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/438,291

(22) Filed: Apr. 3, 2012

(65) Prior Publication Data

US 2012/0276532 A1    Nov. 1, 2012

Related U.S. Application Data

(63) Continuation of application No. 13/099,317, filed on May 2, 2011, now Pat. No. 8,148,116, which is a (Continued)

(51) Int. Cl.
*B01L 7/00* (2006.01)
*C12P 19/34* (2006.01)
(Continued)

(52) U.S. Cl.
CPC .............. *B01L 7/52* (2013.01); *B01L 3/5027* (2013.01); *B01L 3/5082* (2013.01); (Continued)

(58) Field of Classification Search
CPC ........ B01L 7/52; B01L 3/5027; B01L 3/5082; B01L 2200/027; B01L 2200/10; (Continued)

(56) References Cited

U.S. PATENT DOCUMENTS 2,895,475 A    7/1959 Cole
3,036,894 A    5/1962 Forestiere
(Continued)

FOREIGN PATENT DOCUMENTS

DE    2007405    10/1970
DE    2753865    6/1979
(Continued)

OTHER PUBLICATIONS

Alon, et al, "The Kinetics of L-selectin Tethers and the Mechanics of Selectin-mediated Rolling,", J. Cell Biol., 138 (5); 1169-1180 (1997).
(Continued)

*Primary Examiner* — Michael Hobbs
(74) *Attorney, Agent, or Firm* — Pamela C. Ancona; Jeffery P. Bernhardt

(57) ABSTRACT

Provided herein is a sample processing apparatus including a sample-containing vessel and a thermal cycling apparatus, wherein the vessel has at least 3 fluidically isolated segments that are each thermally conductive, compressible, and expandable. The thermal cycling unit is capable of amplifying extracted nucleic acid and has at least a first processing station and a second processing station, each processing station defining a temperature zone, wherein thermal cycling is performed by alternatively transferring the contents of the sample vessel between the at least two processing stations.

19 Claims, 15 Drawing Sheets

Related U.S. Application Data continuation of application No. 11/280,801, filed on Nov. 15, 2005, now Pat. No. 7,935,504, which is a continuation of application No. 10/920,134, filed on Aug. 16, 2004, now Pat. No. 6,964,862, which is a continuation of application No. 09/782,732, filed on Feb. 13, 2001, now Pat. No. 6,780,617.

(60) Provisional application No. 60/259,025, filed on Dec. 29, 2000.

(51) Int. Cl.
*B01L 3/00* (2006.01)
*G01N 35/10* (2006.01)

(52) U.S. Cl.
CPC ..... *B01L 2200/027* (2013.01); *B01L 2200/10* (2013.01); *B01L 2300/0816* (2013.01); *B01L 2300/0832* (2013.01); *B01L 2300/0874* (2013.01); *B01L 2300/1822* (2013.01); *B01L 2300/1861* (2013.01); *B01L 2400/0421* (2013.01); *B01L 2400/0481* (2013.01); *B01L 2400/0655* (2013.01); *G01N 35/1002* (2013.01); *Y10T 436/2575* (2015.01)

(58) Field of Classification Search
CPC ..... B01L 2300/0816; B01L 2300/0832; B01L 2300/0874; B01L 2300/1822; B01L 2300/1861; B01L 2400/0421; B01L 2400/0481; B01L 2400/0655; G01N 35/1002; Y10T 436/2575
USPC ... 435/91.2, 287.3, 288.7, 303.1, 304.2, 809
See application file for complete search history.

(56) References Cited

U.S. PATENT DOCUMENTS

| | | | |
|---|---|---|---|
| 3,441,205 A | 4/1969 | Young, Jr. | |
| 3,556,731 A | 1/1971 | Martin | |
| 3,579,303 A | 5/1971 | Pickering | |
| 3,607,097 A | 9/1971 | Auphan et al. | |
| 3,620,678 A | 11/1971 | Guigan et al. | |
| 3,697,227 A | 10/1972 | Goldstein et al. | |
| 3,698,822 A * | 10/1972 | Polanyi | 356/246 |
| 3,736,933 A | 6/1973 | Szabo | |
| 3,819,158 A | 6/1974 | Sharpe et al. | |
| 3,888,629 A | 6/1975 | Bagshawe et al. | |
| 3,918,913 A | 11/1975 | Stevenson et al. | |
| 4,038,030 A | 7/1977 | Albright et al. | |
| 4,065,263 A | 12/1977 | Woodbridge, III | |
| RE29,725 E | 8/1978 | Johnson et al. | |
| 4,166,457 A | 9/1979 | Jacobsen et al. | |
| 4,187,861 A | 2/1980 | Heffernan | |
| 4,267,149 A | 5/1981 | Bruckner et al. | |
| 4,329,698 A | 5/1982 | Smith | |
| 4,426,451 A | 1/1984 | Columbus | |
| 4,430,139 A | 2/1984 | Baverstock et al. | |
| 4,446,232 A | 5/1984 | Liotta | |
| 4,472,498 A | 9/1984 | Masuda et al. | |
| 4,596,271 A | 6/1986 | Brundage | |
| 4,608,275 A | 8/1986 | Kukanskis et al. | |
| 4,695,430 A | 9/1987 | Coville et al. | |
| 4,752,449 A | 6/1988 | Jackson et al. | |
| 4,803,154 A | 2/1989 | Uo et al. | |
| 4,820,297 A | 4/1989 | Kaufman et al. | |
| 4,822,568 A | 4/1989 | Tomita et al. | |
| 4,846,005 A | 7/1989 | Bacehowski et al. | |
| 4,900,321 A | 2/1990 | Kaufman et al. | |
| 4,917,864 A | 4/1990 | Marsoner et al. | |
| 5,019,348 A | 5/1991 | Ohms et al. | |
| 5,057,438 A | 10/1991 | Imai et al. | |
| 5,061,445 A | 10/1991 | Zoski et al. | |
| 5,073,484 A | 12/1991 | Swanson et al. | |
| 5,087,425 A | 2/1992 | Flossdorf et al. | |
| 5,089,233 A | 2/1992 | DeVaney, Jr. et al. | |
| 5,098,660 A | 3/1992 | Devaney, Jr. | |
| 5,120,662 A | 6/1992 | Chan et al. | |
| 5,143,084 A | 9/1992 | Macemon et al. | |
| 5,176,203 A | 1/1993 | Larzul et al. | |
| 5,178,832 A | 1/1993 | Phillips et al. | |
| 5,185,127 A | 2/1993 | Vonk | |
| 5,187,084 A | 2/1993 | Hallsby | |
| 5,229,297 A | 7/1993 | Schnipelsky et al. | |
| 5,244,813 A | 9/1993 | Walt et al. | |
| 5,258,314 A | 11/1993 | Skerratt | |
| 5,270,183 A | 12/1993 | Corbett et al. | |
| 5,356,785 A | 10/1994 | McMahon et al. | |
| 5,374,395 A | 12/1994 | Robinson et al. | |
| 5,380,665 A | 1/1995 | Cusack et al. | |
| 5,391,478 A | 2/1995 | Greene et al. | |
| 5,422,271 A | 6/1995 | Chen et al. | |
| 5,424,220 A | 6/1995 | Goerlach-Graw et al. | |
| 5,430,957 A | 7/1995 | Eigen et al. | |
| 5,455,175 A | 10/1995 | Wittwer et al. | |
| 5,460,780 A | 10/1995 | Devaney, Jr. et al. | |
| 5,475,610 A | 12/1995 | Atwood et al. | |
| 5,491,067 A | 2/1996 | Setcavage et al. | |
| 5,504,007 A | 4/1996 | Haynes | |
| 5,508,197 A | 4/1996 | Hansen et al. | |
| 5,567,617 A | 10/1996 | Caprio et al. | |
| 5,571,410 A | 11/1996 | Swedberg et al. | |
| 5,576,218 A | 11/1996 | Zurek et al. | |
| 5,591,573 A | 1/1997 | Whalen et al. | |
| 5,602,756 A | 2/1997 | Atwood et al. | |
| 5,626,732 A | 5/1997 | Allington | |
| 5,631,683 A | 5/1997 | Nishioka et al. | |
| 5,645,801 A * | 7/1997 | Bouma et al. | 422/68.1 |
| 5,656,501 A | 8/1997 | Yedgar et al. | |
| 5,668,330 A | 9/1997 | Bartlett-Hooker et al. | |
| 5,709,668 A | 1/1998 | Wacks | |
| 5,714,380 A | 2/1998 | Neri et al. | |
| 5,735,824 A | 4/1998 | Hjertman et al. | |
| 5,736,106 A | 4/1998 | Ishiguro et al. | |
| 5,780,222 A | 7/1998 | Peddada et al. | |
| 5,795,547 A | 8/1998 | Moser et al. | |
| 5,801,052 A | 9/1998 | Bartlett-Hooker et al. | |
| 5,810,778 A | 9/1998 | Hjertman et al. | |
| 5,827,480 A | 10/1998 | Haff et al. | |
| 5,830,411 A | 11/1998 | Martinell Gisper-Sauch et al. | |
| 5,847,734 A | 12/1998 | Pawlowski, Jr. | |
| 5,863,502 A | 1/1999 | Southgate et al. | |
| 5,866,366 A | 2/1999 | Kallender | |
| 5,897,842 A | 4/1999 | Dunn et al. | |
| 5,942,432 A | 8/1999 | Smith et al. | |
| 5,985,651 A | 11/1999 | Hunicke-Smith | |
| 6,016,683 A | 1/2000 | Betts et al. | |
| 6,019,945 A | 2/2000 | Ohishi et al. | |
| 6,033,880 A | 3/2000 | Haff et al. | |
| 6,066,296 A | 5/2000 | Brady et al. | |
| 6,068,751 A | 5/2000 | Neukermans | |
| 6,159,727 A | 12/2000 | Bochkariov | |
| 6,163,714 A | 12/2000 | Stanley et al. | |
| 6,174,670 B1 | 1/2001 | Wittwer et al. | |
| 6,180,698 B1 | 1/2001 | Porter et al. | |
| 6,186,982 B1 | 2/2001 | Gross et al. | |
| 6,190,416 B1 | 2/2001 | Choteau et al. | |
| 6,194,160 B1 | 2/2001 | Levin | |
| 6,210,036 B1 | 4/2001 | Eberle et al. | |
| 6,210,369 B1 | 4/2001 | Wilmot et al. | |
| 6,210,958 B1 | 4/2001 | Brust et al. | |
| 6,250,166 B1 | 6/2001 | Dingwell et al. | |
| 6,251,660 B1 * | 6/2001 | Muir et al. | 435/287.2 |
| 6,264,892 B1 | 7/2001 | Kaltenbach et al. | |
| 6,274,726 B1 | 8/2001 | Laugharn, Jr. et al. | |
| 6,290,960 B1 | 9/2001 | Kink et al. | |
| 6,299,601 B1 | 10/2001 | Hjertman et al. | |
| 6,300,138 B1 | 10/2001 | Gleason et al. | |
| 6,300,308 B1 | 10/2001 | Schroit | |
| 6,303,083 B1 | 10/2001 | Johnson et al. | |
| 6,318,191 B1 | 11/2001 | Chen | |
| 6,439,759 B1 | 8/2002 | Ray et al. | |
| 6,440,072 B1 | 8/2002 | Schuman et al. | |

(56) References Cited

U.S. PATENT DOCUMENTS

| | | | |
|---|---|---|---|
| 6,440,725 | B1 | 8/2002 | Pourahmadi et al. |
| 6,748,332 | B2 | 6/2004 | Chen |
| 6,780,617 | B2 * | 8/2004 | Chen .......................... 435/91.2 |
| 6,964,862 | B2 * | 11/2005 | Chen .......................... 435/91.2 |
| 7,337,072 | B2 | 2/2008 | Chen |
| 7,718,421 | B2 | 5/2010 | Chen et al. |
| 7,785,535 | B2 | 8/2010 | Chen et al. |
| 7,799,521 | B2 | 9/2010 | Chen |
| 7,833,489 | B2 | 11/2010 | Chen |
| 7,935,504 | B2 * | 5/2011 | Chen .......................... 435/91.2 |
| 2002/0049557 | A1 | 4/2002 | Chen |
| 2002/0064484 | A1 | 5/2002 | Lin et al. |
| 2003/0049833 | A1 | 3/2003 | Chen et al. |
| 2003/0208105 | A1 | 11/2003 | Newman et al. |
| 2004/0105782 | A1 | 6/2004 | Chen |
| 2004/0161788 | A1 | 8/2004 | Chen et al. |
| 2004/0209331 | A1 | 10/2004 | Ririe |
| 2004/0223878 | A1 | 11/2004 | Chen |
| 2005/0019875 | A1 | 1/2005 | Chen |
| 2006/0154341 | A1 | 7/2006 | Chen |
| 2008/0003564 | A1 | 1/2008 | Chen et al. |
| 2008/0038813 | A1 | 2/2008 | Chen |
| 2010/0218621 | A1 | 9/2010 | Chen et al. |

FOREIGN PATENT DOCUMENTS

| | | |
|---|---|---|
| EP | 0047806 A1 | 3/1982 |
| EP | 0139373 | 5/1985 |
| EP | 0312394 | 4/1989 |
| EP | 0381501 A2 | 8/1990 |
| EP | 0435380 | 7/1991 |
| EP | 0488769 A2 | 6/1992 |
| EP | 0504772 A2 | 9/1992 |
| EP | 0739241 | 10/1996 |
| EP | 0955097 | 11/1999 |
| EP | 1000661 | 5/2000 |
| EP | 1106250 | 6/2001 |
| FR | 1513306 | 2/1968 |
| FR | 2590673 A1 | 5/1987 |
| FR | 2672231 | 8/1992 |
| WO | WO-94/20831 | 9/1994 |
| WO | WO-94/26414 A1 | 11/1994 |
| WO | WO-97/27324 | 7/1997 |
| WO | WO-97/40939 | 11/1997 |
| WO | WO-97/48818 | 12/1997 |
| WO | WO-98/09728 | 3/1998 |
| WO | WO-98/16313 | 4/1998 |
| WO | WO-98/43740 | 10/1998 |
| WO | WO-98/50147 | 11/1998 |
| WO | WO-99/26724 | 6/1999 |
| WO | WO-99/67646 A1 | 12/1999 |
| WO | WO-99/67647 | 12/1999 |
| WO | WO-00/13014 | 3/2000 |
| WO | WO-00/23803 A1 | 4/2000 |
| WO | WO-00/25920 | 5/2000 |
| WO | WO-01/07892 A1 | 2/2001 |
| WO | WO-03/007677 | 1/2003 |

OTHER PUBLICATIONS

Belgrader, P., et al., PCR Detection of Bacteria in Seven Minutes, Science 284, pp. 449-450. Apr. 16, 1999.

Ben-Hur et al., "Photodynamic Treatment of Red Blood Cell Concentrates for Virus Inactivation Enhances Red Blood Cell Aggregation: Protection with Antioxidants," Photochem. and Photobiol., 66(4):509-512 (1997).

Boehringer Mannheim, Lightcycler Instrument, pp. 1-16, Jul. 1998.

Chen, et al., "Enhanced aggregability of red blood cells of β-thalassemia major patients," Am. Physiol. Soc., H1951-1956 (1996).

Chen, et al., "Monitoring of Erythrocyte Aggregate Morphology Under Flow by Computerized Image Analysis," Biorheology, 32(4):498-496 (1995).

Chen, et al., "Monitoring of Red Blood Cell Aggregability in a Flow-Chamber by Computerized Image Analysis," Clin. Hemorheology, 14(4): 497-507 (1994).

Chen, et al., "Red blood cell aggregability is enhanced by physiological levels of hydrostatic pressure", Biochimica et Biophysica Acta 1192, Elsevier Science B.V., 247-252 (1994).

Chen, et al., "Rolling and transient tethering of leukocytes on antibodies reveal specializations of selectins," Proc. Natl. Acad. Sci. USA 94:3172-3177 (1997).

Findlay et all., "Automated Closed-Vessel System . . . " Nov. 9, 1993, pp. 1927-1933.

Intergen, Amplifluor Universal Detection System, Versatile, Quantitative Detection for PCR in Endpoint and Real-time (2001).

Kenneth Mason Publications; "PCR Processor", Research Disclosure, Hampshire, GB, vol. 396 pp. 207-211, (Apr. 1, 1997).

Kenneth Mason Publications; "Simplified PCR Processor and Method", Research Disclosure, Hampshire, GB, vol. 401, pp. 651-655, (Sep. 1, 1997).

Kopp, et al. "Chemical Amplification: Continuous-Flow PCR on a Chip," Science, vol. 280, May 15, 1998.

Rasmussen, et al. "Quantitative PCR by Continuous Fluorescense Monitoring of a Double Strand DNA Specific Binding Dye," Biochemica, No. 2 (1998), pp. 8-11.

Roche Molecular Biochemicals, LightCycler System, Real-time PCR—as flexible as you are, pp. 1-34, Jan. 2000.

Schober, et al. "Multichannel PCR and Serial Transfer Machine as a Future Tool in Evolutionary Biotechnology," Biotechinques 1995, 18:652-661.

Taylor, et al., "Enhanced Human Red Blood Cell Aggregation While Diving," Naval Medical Research Institute, Bethesda, MD and Dept. of Biochemistry, Hebrew University-Hadasseh Medical School, Jerusalem, Israel (1997).

Wittwer, et al. "Minimizing the Time Required for DNA Amplification by Efficient Heat Transfer to Small Samples," Anal Biochem 1990, 186:328-331.

World Wide Web Page, Nalge Nunc International, DIAPOPS, http://nunc.nalgenunc.com/resource/technical/nag/dp0014.htm, pp. 1-4, Oct. 31, 2000.

World Wide Web Page, Quantitation of DNA/RNA Using Real-time PCR Detection, www.appliedbiosystems.com/molecularbiology/about/white.htm/per/sds/ (Applied Biosystems), pp. 1-8, Oct. 31, 2000.

World Wide Web Page, Quantitative Real-Time PCR, www.lsc.psu.edu/stf/naf/quantitative.htm/ (PennState Life Sciences Consortium, Shared Technology Facilities), pp. 1-3, Oct. 31, 2000.

European Examination Report for EP 02775793.9 dated Aug. 30, 2011.

European Search Report for EP 02775793 dated Sep. 17, 2009.

European Examination Report for EP 04737303.0 dated Jul. 2, 2012.

International Search Report for PCT/US1999/14105 dated Oct. 19, 1999.

International Search Report for PCT/US2002/28951 dated Jul. 16, 2002.

International Search Report for PCT/US2001/49707 dated Jul. 8, 2003.

European Search Report for EP 12194999 dated Feb. 20, 2013.

European Examination Report for EP Application No. 04737303.0 dated Mar. 4, 2013.

\* cited by examiner

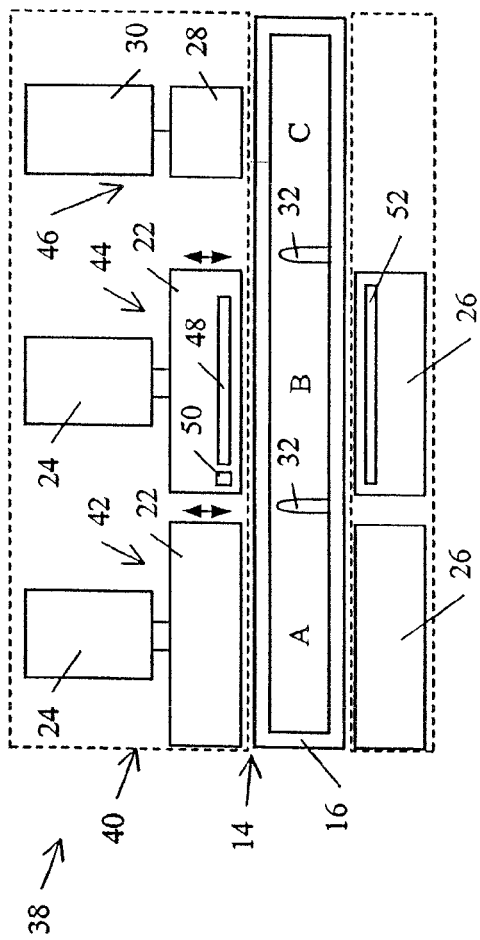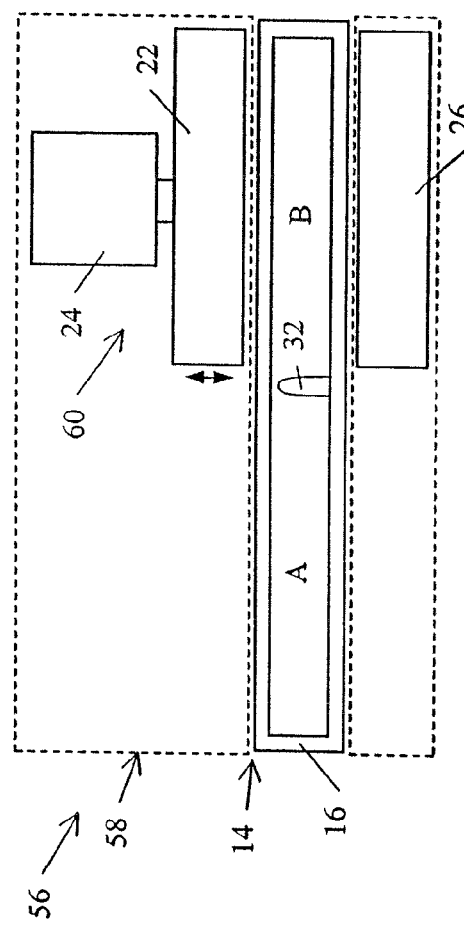

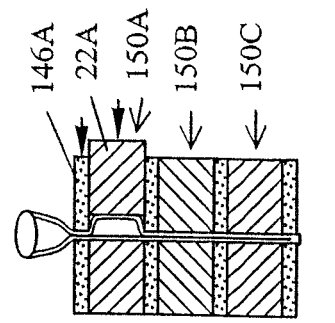
Fig. 13C
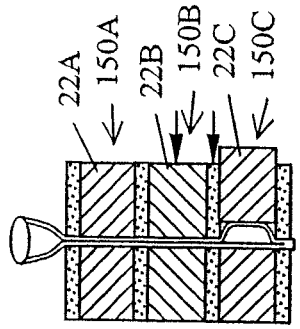
Fig. 13G
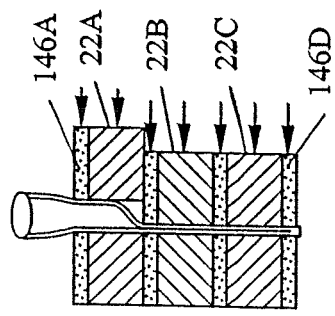
Fig. 13B
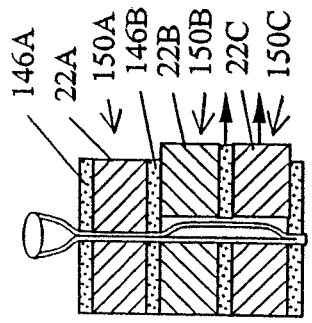
Fig. 13F
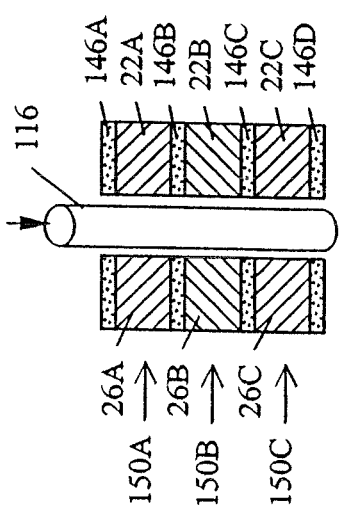
Fig. 13A
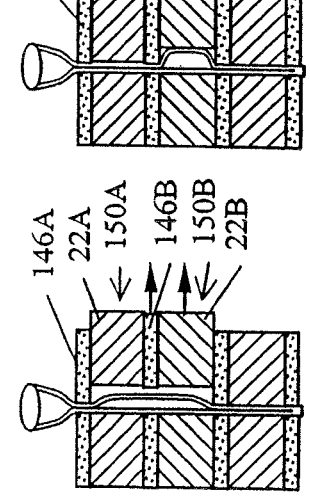
Fig. 13E
Fig. 13D

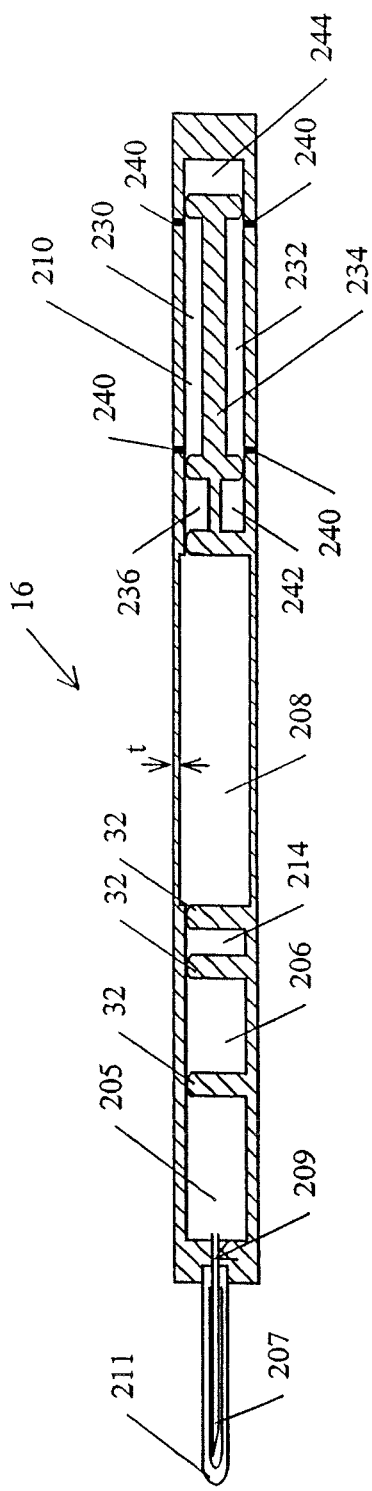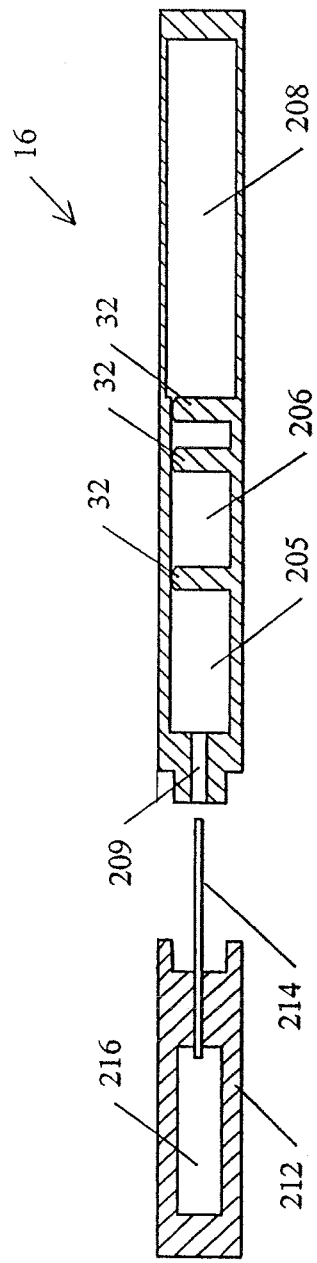
Fig. 15A
Fig. 15B

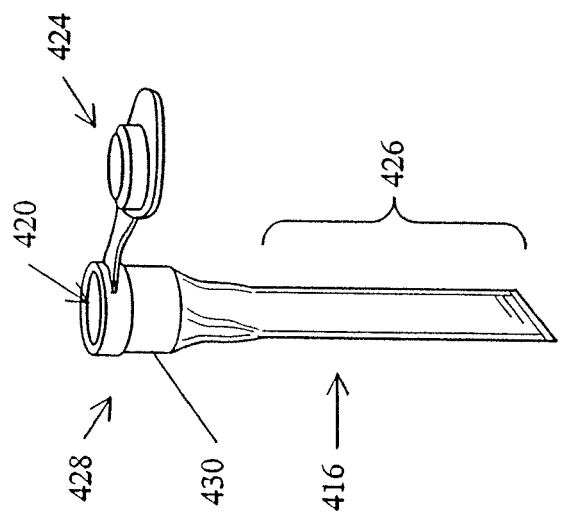

SAMPLE PROCESSING DEVICE FOR PRETREATMENT AND THERMAL CYCLING

CROSS-REFERENCE TO RELATED APPLICATIONS

This application is a continuation of U.S. application Ser. No. 13/099,317, filed May 2, 2011, now U.S. Pat. No. 8,148,116, which is a continuation of U.S. application Ser. No. 11/280,801, filed Nov. 15, 2005, now U.S. Pat. No. 7,935,504, which is a continuation of U.S. application Ser. No. 10/920,134, filed Aug. 16, 2004, now U.S. Pat. No. 6,964,862, which is a continuation of U.S. application Ser. No. 09/782,732, filed Feb. 13, 2001, U.S. Pat. No. 6,780, 617, which claims the benefit of U.S. provisional application Ser. No. 60/259,025, filed Dec. 29, 2000. The contents of the aforementioned applications are hereby incorporated herein by reference.

BACKGROUND

As result of the Human Genome Project and other genetic research, a tremendous amount of genomic and biomarker information is presently available to healthcare providers. Using molecular diagnostic testing, genomic and biomarker information can provide a resource to healthcare providers to assist in the rapid and accurate diagnosis of illness. However, the development of diagnostic testing systems allowing the use of such genetic information, particularly in the clinical setting, has failed to match pace with the genetic research providing the information. Current diagnostic testing systems are mainly limited to large medical testing centers or research labs due to the high costs associated with acquiring and operating the systems and the complexity of the molecular diagnostic assays being employed. These current systems require a large initial capital investment and incur high costs for reagents, disposables, operation, maintenance, service and training.

SUMMARY

The present invention provides sample processing devices and methods that facilitate the rapid analysis of biological samples, such as blood, saliva, or urine, in an efficient and cost effective manner with minimal, if any, exposure to biohazards. The sample processing devices and methods of the present invention are particularly suited to the clinical setting, allowing the clinician to readily proceed from acquisition of a test sample to analysis of the test results, with minimal human intervention. The sample processing devices of the present invention may be implemented as a hand-held system suitable for the processing of a single sample or as a larger, bench top unit suitable for the simultaneous processing of multiple samples. The present invention may be valuable in all diagnostic and therapeutic monitoring areas, including in the point-of-care or clinical setting, in high-throughput screening, and in biological warfare detection. In addition, the present invention provides a sample vessel for holding a biological sample throughout the processing of the sample.

In accordance with one embodiment of the present invention, a device for processing a sample includes a processing unit having an opening to receive a sample vessel and at least one processing station positioned along the opening. The processing station includes a compression member adapted to compress the sample vessel within the opening and thereby displace a content of the sample vessel within the sample vessel. The content displaced by the compression member can be, for example, the sample, a reagent, or a mixture of the content and a reagent In accordance with another aspect, the processing station may include an energy transfer element for transferring energy to or from the content within the sample vessel and a control system coupled to the energy transfer element to control the energy transferred to or from the content. The energy transfer element can be, for example, an electronic heat element, a microwave source, a light source, an ultrasonic source or a cooling element.

In accordance with a further aspect, the energy transfer element transfers thermal energy to or from the content within the sample vessel. An energy insulator may be positioned adjacent the processing station. The energy insulator can be, for example, an energy shielding layer, an energy absorption layer, an energy refraction layer, or a thermal insulator, depending on the type of energy transfer element employed. A temperature sensor may be coupled to the control system to monitor temperature at the processing station. Alternatively, the processing station may include a heat sink to dissipate thermal energy from the processing station.

In accordance with another aspect, the processing station may include a stationary member opposing the compression member across the opening. The compression member can operate to compress the sample vessel against the stationary member within the opening.

In accordance with a further aspect, a driver may be coupled to the compression member to selectively move the compression member and thereby compress the sample vessel within the opening. The driver can be, for example, a motor coupled to the compression member by a cam. Alternatively, the driver can be an electromagnetic actuating mechanism.

In accordance with another aspect, the processing device can include a sensor for detecting a signal from the content within the sample vessel. An energy source can optionally be provided for applying energy to the content within the sample vessel to generate a signal from the content. In one embodiment, the processing device can include an electrophoresis system comprising a pair of electrodes adapted to have a predetermined voltage difference and an electrode actuator for inserting the electrodes into the sample vessel.

In accordance with a further aspect, the processing device may include a reagent injector cartridge actuator adapted to receive a reagent injector cartridge having at least one needle in fluid communication with a reagent reservoir. The reagent injector cartridge actuator can be operable to move the reagent injector cartridge to inject a quantity of reagent into the sample vessel.

In accordance with another embodiment of the invention, a sample vessel for holding a sample includes a sample containing portion for holding the sample and a handling portion for handling the sample vessel. The sample containing portion can have a wall constructed of a flexible material permitting substantial flattening of a selected segment of the sample containing portion. The handling portion can be coupled to the sample containing portion and preferably has a generally rigid construction to facilitate handling of the sample vessel.

In accordance with another aspect, the sample containing portion of the sample vessel can be a tubule.

In accordance with a further aspect, the sample vessel can include at least one pressure gate disposed within the sample containing portion to divide the sample containing portion into a plurality of segments. At least one of the segments of the sample vessel can have a filter contained therein that is structured to separate selected components of a sample material from other components of the sample material. Additionally, at least one of the segments of the sample vessel can contain a reagent. The reagent can be, for example, an anticoagulant, a cell lyses reagent, a nucleotide, an enzyme, a DNA polymerase, a template DNA, an oligonucleotide, a primer, an antigen, an antibody, a dye, a marker, a molecular probe, a buffer, or a detection material. The sample containing portion also can include an electrophoresis segment containing a gel for electrophoresis. The electrophoresis segment can include a pair of electrodes adapted to maintain a predetermined voltage difference therebetween. Additionally, one of the segments can contain multilayer membranes or a micro-array bio-chip for analyzing the sample.

In accordance with another aspect, the sample containing portion can include a self-sealing injection channel formed therein. The self sealing injection channel is preferably normally substantially free of sample material and capable of fluid communication with the sample material in the sample containing portion.

In accordance with another aspect, the sample vessel can include an instrument for obtaining a sample coupled to the sample vessel.

In accordance with a further aspect, the handling portion of the sample vessel includes an opening for receiving a sample. The sample vessel also can include a closure for selective closing the opening. Preferably, the closure seats against the handling portion to close the opening. In addition, the instrument for obtaining a sample can be coupled to the closure of the sample vessel.

In accordance with another aspect, the handling portion has a wall thickness greater than a thickness of the wall of the sample containing portion. Preferably, the thickness of the wall of the sample containing portion is less than or equal to 0.3 mm. In one embodiment, the handling portion can include a cylindrical sleeve sized and shaped to fit over a portion of the sample containing portion. The handling portion is preferably positioned longitudinally adjacent the sample containing portion.

In accordance with another embodiment, a sample vessel for holding a sample includes a sample containing portion having at least one pressure gate disposed within the sample containing portion to divide the sample containing portion into a plurality of segments. Preferably, at least one segment of the sample containing portion has a wall constructed of a flexible material permitting substantial flattening of the segment of the sample containing portion.

In accordance with another embodiment, a method of processing a sample within a sample vessel includes the steps of introducing the sample vessel into a device for processing the sample and compressing the sample vessel to move the sample within the sample vessel from a first segment to a second segment of the sample vessel.

In accordance with another aspect, the method of processing a sample can include the step of introducing a reagent to the sample within a segment of the sample vessel.

In accordance with a further aspect, the method of processing a sample can include the step of heating the sample in the first segment to a first temperature. The method can also include the step of heating the sample to a second temperature in the second segment. In one embodiment, the first temperature can be effective to denature the sample and the second temperature is one at which nucleic acid annealing and nucleic acid synthesis can occur. The method of processing a sample can further include the steps of compressing the sample vessel to move the sample within the sample vessel from the second segment to the first segment of the sample vessel and heating the sample to the first temperature in the first segment.

In accordance with another aspect, the method of processing the sample can include the step of analyzing the sample by detecting a signal from the sample within a segment of the sample vessel and analyzing the detected signal to determine a condition of the sample. The analyzing step can include applying an excitation energy to the sample within the segment of the sample vessel. Additionally, the analyzing step can include conducting electrophoresis analysis of the sample by applying a selective voltage to the sample within a segment of the sample vessel, detecting light emitted from the sample, and analyzing the detected light to determine a condition of the sample.

Alternatively, the analyzing step can include applying an excitation energy to a bio-array member contained within a segment of the sample vessel, detecting light emitted from the bio-array member, and analyzing the detected light to determine a condition of the sample. The bio-array member can be, for example, a multi-layer membrane or a micro-array bio-chip.

In accordance with a further aspect, the method of processing a sample can include the step of agitating the sample within a segment of the sample vessel.

In accordance with another embodiment, a method of treating a sample within a sample vessel can include the steps of introducing the sample vessel into a device for processing the sample within the sample vessel and compressing one of the segments to mix the reagent with the sample within the sample vessel. Preferably, the sample vessel has a plurality of segments including a segment for containing a reagent and a segment for containing the sample.

In accordance with another aspect, the method of processing the sample can include the step of introducing the reagent into a reagent segment of the sample after the step of introducing the sample vessel into the device for processing the sample.

In accordance with another embodiment, a thermal cycler includes a processing unit having an opening to receive a sample vessel containing a sample. The processing unit can have a first processing station, a second processing station, and a third processing station positioned along the opening. The first processing station can include a first compression member adapted to compress the sample vessel within the opening and a first energy transfer element for transferring energy to the sample at the first processing station. The second processing station can include a second compression member adapted to compress the sample vessel within the opening and a second energy transfer element for transferring energy to the sample at the second processing station. The third processing station can include a third compression member adapted to compress the sample vessel within the opening and a third energy transfer element for transferring energy to the sample at the third processing station. Compression of the sample vessel by of one of the compression members can displace the sample within the sample vessel between the processing stations.

BRIEF DESCRIPTION OF THE DRAWINGS

These and other features and advantages of the present invention will be more fully understood by reference to the following detailed description in conjunction with the attached drawings in which like reference numerals refer to like elements through the different views. The drawings illustrate principles of the invention and, although not to scale, show relative dimensions.

FIG. 1 is a schematic diagram of a device for processing a sample according to the present invention;

FIG. 3 is a schematic diagram of an alternative embodiment of a device for processing a sample according to the present invention;

FIG. 4 is a schematic diagram of an alternative embodiment of a device for processing a sample according to the present invention;

FIGS. 13A-13G are side elevational views, in cross-section, of a processing unit of the present invention, illustrating the operation of the processing unit;

FIGS. 15A-15B are side elevational views, in cross-section, of embodiments of a sample vessel according to the present invention;

FIG. 18 is a side elevational view, in cross-section, of a sample vessel according to the present invention.

DETAILED DESCRIPTION OF CERTAIN PREFERRED EMBODIMENTS

Figure 1:
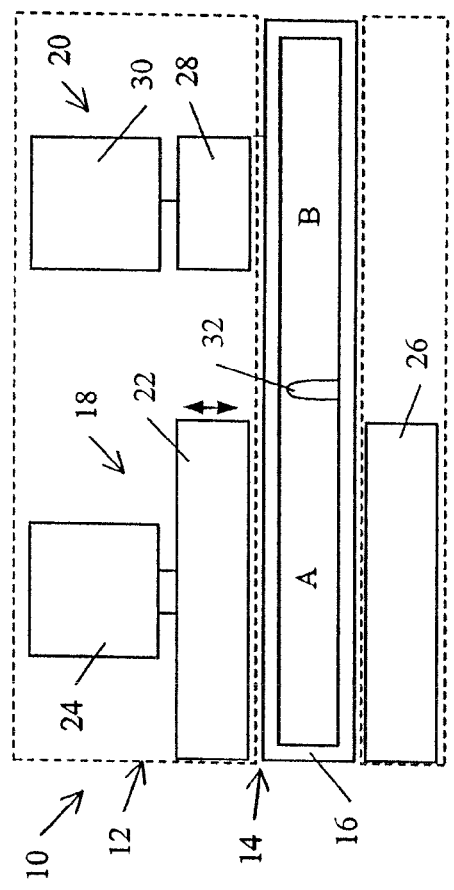

The present invention provides devices and methods for processing a sample. The term "processing" as used herein generally refers to the preparation, treatment, analysis, and/or the performance of other testing protocols or assays on a content of the sample vessel in one or more steps. Exemplary processing steps include, for example: displacing a content, e.g., the sample or a reagent, of the sample vessel within the sample vessel to, for example, adjust the volume of the content, separate content components, mix contents within the sample vessel; effecting a chemical or biological reaction within a segment of the sample vessel by, for example, introducing a reagent to the sample, agitating the sample, transferring thermal energy to or from the sample, incubating the sample at a specified temperature, amplifying components of the sample, separating and/or isolating components of the sample; or analyzing the sample to determine a characteristic of the sample, such as, for example, the quantity, volume, mass, concentration, sequence, or nucleic acid size or other analyte size, of the sample. One skilled in the art will appreciate that the forgoing exemplary processing steps are described herein for illustrative purposes only. Other processing steps may be employed without departing from the scope of the present invention.

A device for processing a sample according to the present invention can integrate one or more processing units into a single system depending on the process being employed. The processing units can include one or more processing stations at which one or more processing steps can be performed on the sample within the sample vessel. Sample materials that can be processed according to the present invention are generally biological samples or samples containing biological substance and include, for example, blood, urine, saliva, cell suspensions, biofluids, a piece of tissue, soil or other samples. A sample processing device of the present invention is particularly suited for nucleic acid amplification, such as polymerase chain reaction (PCR) or ligase chain reaction (LCR) amplification, and can include, for example, a sample pretreatment unit for extracting nucleic acid from sample, a thermal cycling reaction unit for amplification of the nucleic acid or signal, and (optionally) an analysis or detection unit for analyzing the amplified product. The sample processing device of the present invention can also be used for isothermal reaction of nucleic acid or signal amplifications, such as strand displacement amplification (SDA), rolling circle amplification (RCA), and transcription-mediated amplification (TMA). Other exemplary processes to be performed on samples can include clinical diagnosis, therapeutic monitoring, and screening of chemical compounds for discovery of new drugs. The following description primarily focuses on PCR amplification for illustration. However, one skilled in the art will appreciate that the devices and methods of the present invention are not limited to PCR amplification, as the devices and methods described below can be employed in other sample processing.

An exemplary embodiment of a device for processing a sample is illustrated in FIG. 1. The processing device 10 illustrated in FIG. 1 includes a processing unit 12 having an opening 14 to receive a sample vessel 16. The opening 14 can be a tubular shaped opening, an open-faced slot or other structure for receiving the sample vessel 16 in a removable and replaceable manner. The processing unit 12 includes a first processing station 18 and a second processing station 20, each positioned along the length of the opening 14. The first processing station 18 includes a compression member 22 adapted to compress the sample vessel 16 within the opening 14 and thereby displace a content of the sample vessel within the sample vessel 16. The content of the sample vessel can be, for example, the sample, a reagent contained within the sample vessel, or a mixture of the sample and the reagent. A driver 24 is coupled to the compression member 22 to selectively move the compression member 22 and thereby compress the sample vessel 16 within the opening 14. The driver 24 can be, for example, an electromagnetic actuating mechanism, a motor, a solenoid, or any other device for imparting motion, preferably reciprocal motion, to the compression member 22, as described in further detail below.

Preferably, the compression member 22 is constructed from a rigid material such as a rigid plastic or a metal. The compression member can be constructed in any shape sufficient to impart a compressive force on the sample vessel. For example, the compression member 22 can be a block having a rectilinear, planar surface for engaging the sample vessel 16, as illustrated in FIG. 1. Alternatively, the compression member can have a curved, angular, or non-planar surface for engaging the sample vessel 16.

Moreover, the compression member 22 alternatively can be an inflatable membrane that can be inflated by a fluid, e.g., air, nitrogen, saline, or water, to impart a compressive force on the sample vessel. In this embodiment, the amount of compression of the sample vessel may be controlled by the adjusting the inflation pressure of the membrane.

Figure 2:
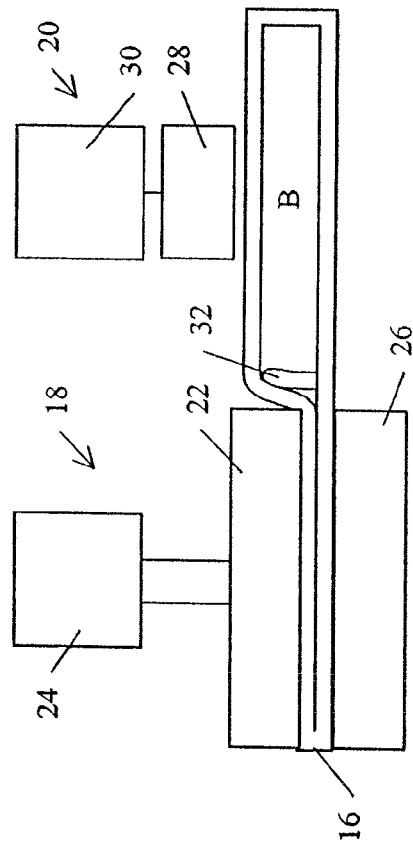
FIG. 2 is a schematic diagram of the device of FIG. 1, illustrating a compression member of a processing station of the device compressing the sample vessel.

The first processing station 18 can optionally include a stationary member 26 positioned opposite the compression member 22 across the opening 14. The compression member 22, thus, can compress a portion of the sample vessel 16 within the opening 14 against the stationary member 26, as illustrated in FIG. 2. One skilled in the art will appreciate that the stationary member 26 may be replaced with a second compression member, such that the processing station includes two compression members that move together to compress the sample vessel therebetween. In addition, a stationary member or second compression member may be omitted by securing the sample vessel 16 within the opening on either side of the compression member.

In the illustrated embodiment, the sample vessel 16 is a closed tubule flow-chamber for holding the sample. Preferably, one or more segments of the sample vessel 16 are constructed of a flexible, compressible material, such as, for example, polyethylene or polyurethane, to allow selective compression, and preferably flattening, of the sample vessel to move the sample, or other contents of the sample vessel, within the sample vessel, preferably while the sample vessel 16 remains in the device 10. In one preferred embodiment, the sample vessel 16 includes a plurality of segments separated by an integral, internal structure, such as a microfluidic pressure gate, as described in more detail below. Alternatively, the sample vessel 16 can be constructed without internal, integral structures to form segments and the device 10 can be utilized to segment the sample vessel by compressing selective portions of the sample vessel. One skilled in the art will appreciate that other types of sample vessels suitable for containing a sample may be used with the device 10 without departing from the scope of the present invention.

The second processing station 20 can include a sensor 28 for detecting a signal from the content, e.g., the sample or a reagent, of the sample vessel 16. For example, the sensor 28 can be an optical sensor for measuring light, for example fluorescent light, emitted from the sample or from fluorescent probes within the sample. In addition, multiple sensors or a spectrum sensor can be used when detection of multiple wavelength light is required. The detected signal can be sent to a CPU 30 to analyze the detected signal and determine a characteristic of the sample.

In operation, a sample can be introduced to a first segment A of the sample vessel 16 by injecting the sample through the walls of the sample vessel 16 or by introducing the sample through an opening formed in the sample vessel 16, as described in more detail below. In the present exemplary embodiment illustrated in FIGS. 1 and 2, the sample vessel 16 includes a pressure gate 32 that divides the sample vessel 16 into a first segment A and a second segment B. The sample vessel 14 can be inserted into the opening 14 of the device 10 such that the first segment A of the sample vessel 16 is aligned with the first processing station 18 and the second segment B is aligned with the second processing station 20, as illustrated in FIG. 1.

The driver 24 can operate to move the compression member 22 into contact with the sample vessel 16 such that the first segment A of the sample vessel 16 is compressed within the opening 14 between the compression member 22 and the stationary member 26. As the first segment A of the sample vessel 16 is compressed, a quantity of sample is displaced from the first segment A to the second segment B through the pressure gate 32. The volume of sample displaced is proportional to the amount of compression of the first segment A by the compression member 22. Thus, the compression member 22 of the first processing station 18 can be used to displace a specific quantity of sample into the second segment B of the sample vessel 16 for analysis at the second processing station 20. Substantially all of the sample can be displaced from the first segment A of the sample vessel 16 by completely flattening the first segment A of the sample vessel 16, as illustrated in FIG. 2. The sample can be analyzed in the second segment B of the sample vessel 16 at the second processing station 20.

An alternative embodiment of a device for processing a sample is illustrated in FIG. 3. The device 38 includes a processing unit 40 having three processing stations positioned along the opening 14, namely, a first process station 42, a second processing station 44 adjacent the first processing station 42, and a third processing station 46 adjacent the second processing station 44.

The first processing station 42 includes a compression member 22 coupled to a driver 24 and adapted to compress a segment of the sample vessel 16 against a stationary member 26 within the opening 16. The first processing station 42 can operate to displace a selective quantity of the sample from a first segment A of the sample vessel into other segments of the sample vessel.

The second processing station 44 includes a compression member 22 coupled to a driver 24 and adapted to compress a second segment B of the sample vessel 16 against a stationary member 26 within the opening 16. The second processing station 44 includes an energy transfer element 48 for transferring energy to or from the contents of the sample vessel 16. The energy transfer element 48 can be, for example, an electronic heat element, a microwave source, a light source, an ultrasonic source, a cooling element, or any other device for transferring energy. In one embodiment, the energy transfer element 48 transfers thermal energy to or from the sample within the sample vessel. The energy transfer element 48 can be embedded in or otherwise coupled to the compression member 22, as illustrated in FIG. 3. Alternatively, the energy transfer element 48 can be coupled to the stationary member 26 or can be positioned within the processing station independent of the compression member or the stationary member. The energy transfer element 48 can be coupled to a control system that controls the energy transferred to or from the sample vessel 16 by the energy transfer element 48. The control system can be a component system of the CPU 30 or can be an independent system. The control system can also include a temperature sensor 50 to monitor the temperature of the energy transfer element.

The second processing station 44 also can include a sensor 52 for detecting a signal from the content of the sample vessel, particularly during processing in the second processing station. For example, the sensor 52 can be an optical sensor for measuring light, for example fluorescent light, emitted from the sample or from fluorescent probes within the sample. The sensor 52 can be coupled to the CPU 30 for analysis of the detected signal to determine a characteristic of the sample.

The third processing station 46 can include a sensor 28 for detecting a signal from the content, e.g., the sample or a reagent, of the sample vessel 16. For example, the sensor 28 can be an optical sensor for measuring light, for example fluorescent light, emitted from the sample or from fluorescent probes within the sample. In addition, multiple sensors or a spectrum sensor can be used when detection of multiple wavelength light is required. The detected signal can be sent to a CPU 30 to analyze the detected signal and determine a characteristic of the sample.

In operation, a sample can be introduced into a first segment A of the sample vessel 16 and the sample vessel 16 can be introduced into the opening 14 of the device 10. In the embodiment illustrated in FIG. 3, the sample vessel 16 includes two pressure gates 32 that divide the sample vessel 16 into three segments, namely, the first segment A, a second segment B, and a third segment C. The first processing station 42 can operate to displace a selective amount of the sample into the second segment B of the sample vessel 16 for processing at the second processing station 44.

At the second processing station 44, energy can be transferred to or from the sample within the second segment B. In this manner, a biological or chemical reaction involving the sample may be carried out in the second segment B. The sensor 52 can be used to monitor the reaction during the reaction process.

Upon completion of the reaction, the sample can be moved into the third segment C of the sample vessel 16 by compressing the sample vessel 16 within the opening at the second processing station 44. Preferably, the compression member 22 of the first processing station 42 substantially flattens the first segment A of the sample vessel 16 to inhibit the sample from entering the first segment A. The sample can be analyzed in the third segment C of the sample vessel 16 at the third processing station 46.

A further embodiment of a device for processing a sample is illustrated in FIG. 4. The device 56 includes a processing unit 58 having a processing station 60 positioned along the opening 14. The processing station 60 includes a compression member 22 coupled to a driver 24 and adapted to compress a segment of the sample vessel 16 against a stationary member 26 within the opening 16. In the embodiment illustrated in FIG. 4, the sample vessel 16 includes a pressure gate 32 that divides the sample vessel 16 into two segments, namely, a first segment A and a second segment B. The processing station 60 can operate to displace a selective quantity of the content from the second segment B of the sample vessel into the first segment A of the sample vessel. For example, a reagent can be introduced into the second segment B of the sample vessel 16. A quantity of reagent can be displaced from the second segment B into the first segment A of the sample vessel 16 to mix with the sample in the first segment A. Alternatively, the reagent can be introduced into the first segment A of the sample vessel 16 and a quantity of the sample can be displaced from the second segment B into the first segment A by the processing station 60. Thus, the first segment A of the sample vessel can act as a reaction mixture chamber for the sample and the reagent. The reagent can be pre-packaged in the sample vessel 16 or can be introduced to the sample vessel 16 after the sample is introduced to the sample vessel 16. For example, the reagent can be introduced using a reagent injector cartridge, described below, that is included with the device.

Figure 5:
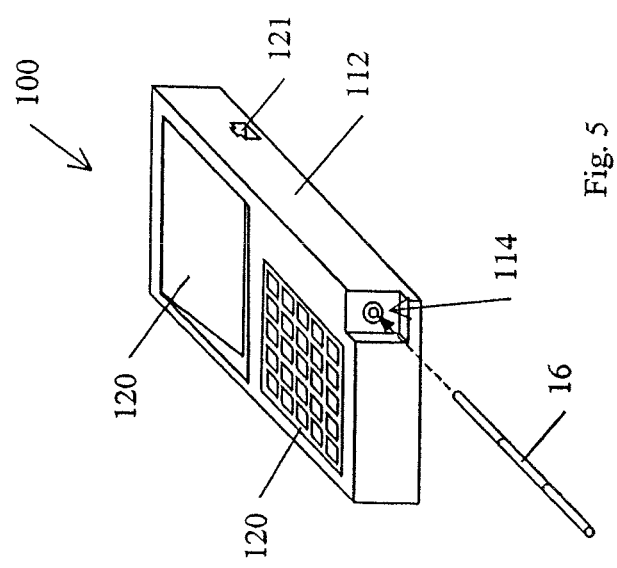
FIG. 5 is a perspective view of an embodiment of a hand held device for processing a sample according to the present invention.

Referring to FIG. 5, another embodiment of device for processing a sample is illustrated. The illustrated device 100 is a hand held system for processing a nucleic acid sample, preferably in an "insert and test" format in which a sample vessel containing a nucleic acid sample is inserted into the device 100 and processing results are produced by the device with minimal human intervention. The device 100 can include a housing 112 having an opening 114 for receiving a sample vessel 116 containing a sample for processing by the device 100. The opening 114 can be a tubular shaped opening, as illustrated in FIG. 5, or can be an open-faced slot or other structure for receiving the sample vessel in a removable and replaceable manner. A control panel 118 is located on the top of the housing 112 for inputting information to the device 100 and a monitor 120 is provided for displaying operating information, such as the results of processing. An external communication port 121 can be located on the housing 112 for receiving information or outputting information, such as the results of processing and remote diagnosing of the system, to a remote system, such as a computer network. A battery 123 (FIG. 7) can be located within the housing to provide electrical power to the components of the device 100.

Figure 6:
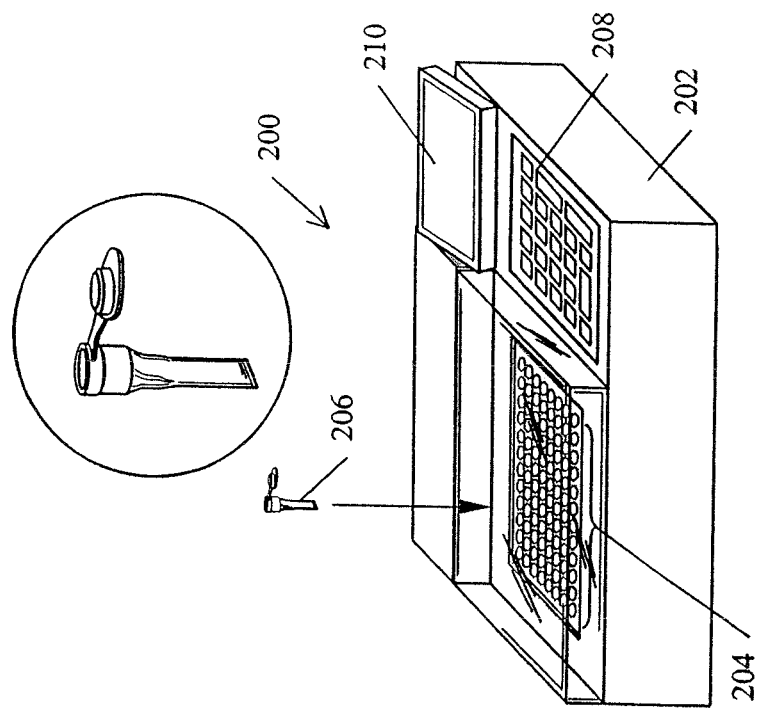
FIG. 6 is a perspective view of an embodiment of a bench top device for processing a sample according to the present invention.

A multi-sample device 200 for processing multiple samples is illustrated in FIG. 6. The device 200 is a bench top thermal cycling system for processing up to 96 nucleic acid samples simultaneously. The sample processing device 200 operates on the same principles as the sample processing device 100 illustrated in FIG. 5, except that the multi-sample device 200 provides increased capacity and throughput. The multi-sample processing device 200 can include a housing 202 having a plurality of wells or openings 204, with each well being capable of receiving a sample vessel 206 containing a sample for processing by the device. The exemplary multi-sample device 200 illustrated in FIG. 6 has ninety-six wells for treating up to 96 samples simultaneously. One skilled in the art will appreciate that a multi-sample processing device according to the present invention may be designed with any number of wells, depending on the sample being tested and the processes being employed, without departing from the scope of the present invention. A control panel 208 is located on the top of the housing 202 for inputting information to the multi-sample processing device 200 and a monitor 210 is provided for displaying operating information, such as the results of testing.

Figure 7:
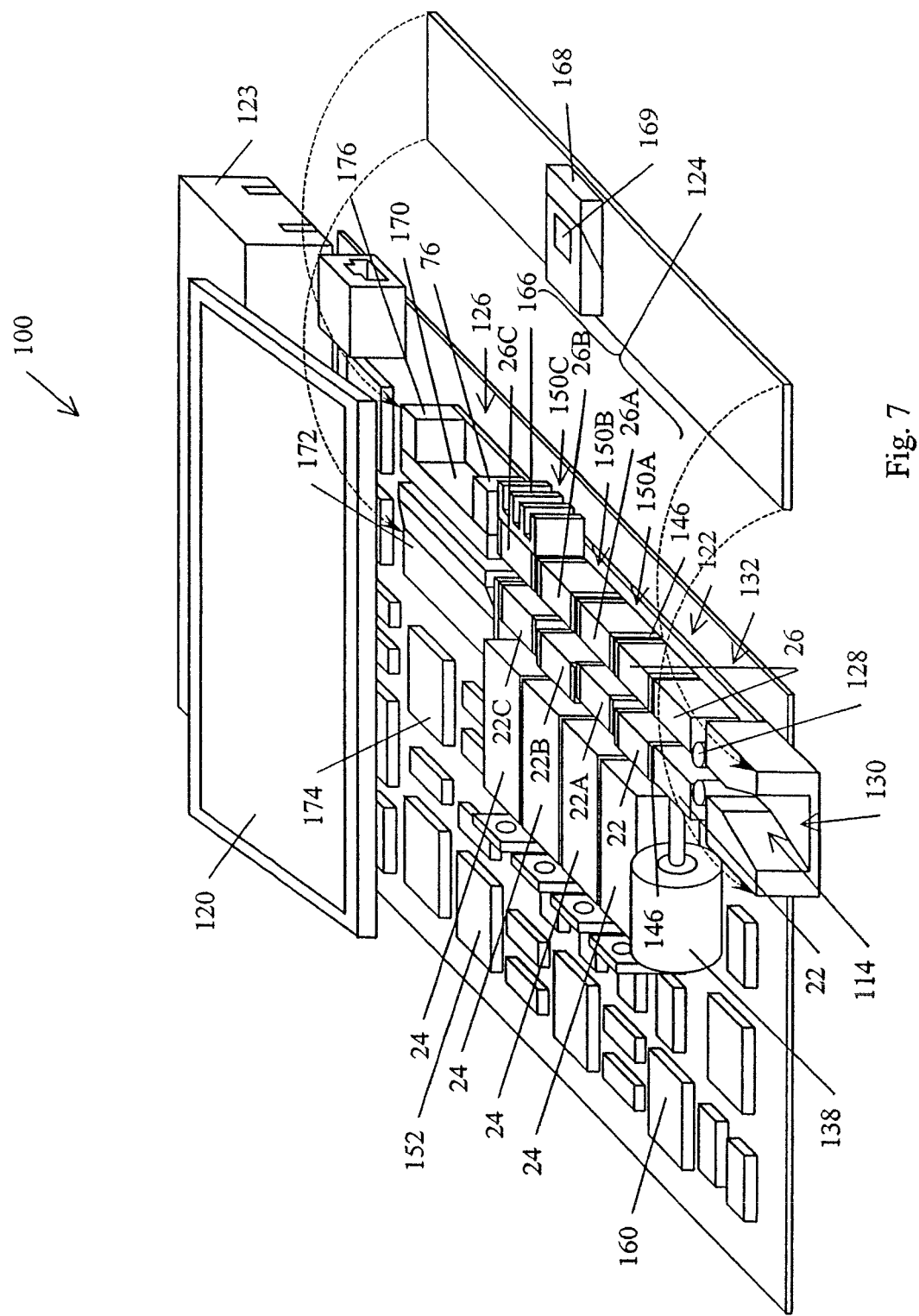
FIG. 7 is a perspective view of the device of FIG. 6, illustrating the device with the top cover removed.

FIG. 7 illustrates the general components of the sample processing device 100 illustrated in FIG. 5. The illustrated device 100 includes three primary processing units for processing a sample within the sample vessel, namely, a pretreatment unit 122 for pretreating the sample, a reaction unit 124 for amplifying certain components of the sample, and an analysis unit 126 for analyzing the sample. The sample vessel can be loaded into the device 100 through the opening 114. The processing units of the device are preferably arranged along the axis of elongation of the opening 114. This arrangement allows the sample to be moved within the sample vessel between the processing units of the device 100 in a manner described in detail below. Preferably, the processing units are arranged linearly as illustrated in FIG. 7, however, other arrangement are possible so long as the sample vessel can be positioned adjacent one or more of the processing units of the device 100.

Continuing to refer to FIG. 7, a pair of sample vessel loading wheels 128 is located at the entrance 130 of the sample vessel opening 114. The entrance 130 is preferably tapered to facilitate loading of the sample vessel into the opening 114 of the device 100. The loading wheels 128 further facilitate loading of the sample vessel by guiding the sample vessel into the opening 114. A sample collection unit 132 can be positioned proximate the entrance 130 of the opening 114 to allow a selective volume of the sample to dispense into the next processing unit or units within the sample vessel. The sample collection unit 132 can include a compression member 22 opposed to a stationary member 26 across the width of the opening 114. A linear motor 138 is coupled to the compression member 22. The linear motor 138 can operate to move the compression member 22 toward or away from the stationary member 26 to selectively open and close the opening 114 therebetween. When the sample vessel is positioned within the opening 114, the linear motor 138 can operate to compress the sample vessel between the compression member 22 and the stationary member 26. As a result, a selective volume of the sample can be moved to the next processing unit within the sample vessel. Preferably, the sample vessel remains compressed between the compression member 22 and the stationary member 26 of the sample collection unit 132 during processing of the sample by the other processing units to prevent the sample from exiting the processing unit area during processing.

The pretreatment unit 122 is positioned adjacent the initial sample collection unit 132. Depending on the process being implemented, the sample may require pretreatment or preparation before proceeding with additional processing steps. Pretreatment can include, for example, adding a reagent or other material to the sample and incubating the mixture for certain time period. The pretreatment unit 122 of the device 100 allows for any of such pretreatment steps to be implemented. For PCR testing, the sample pretreatment unit 122 can provide for nucleic acid extraction from a biological sample, such as blood. Any known methods for extracting nucleic acid can be utilized in the pretreatment unit, including using a cell lysis reagent, boiling the nucleic acid sample, GITC, or formamide for solubilization. Alternatively, filters can be used within the sample vessel to separate nucleic acid from unwanted cellular debris.

The pretreatment unit 122 can include a compression member 22 and a stationary member 26 opposed to the compression member 26 across the opening 114. The compression member 22 and/or the stationary member 26 can optionally include an energy transfer element for transferring energy, e.g. thermal energy, to the sample within the sample vessel. The energy transfer element can be, for example, an electronic heat element (such as Kapton heater, a Nomex heater, a Mica heater, or a silicone rubber heater), a microwave generator, a light source, an electronic cooling element (such as Peltier element), an ultrasonic energy transfer element, or any another device suitable for transferring thermal energy. A driver 24, for example an electromagnetic actuator such as linear stepper actuator, a relay actuator, or a solenoid, is coupled to the compression member 22 and operates as a driver. During operation of the pretreatment unit 122, the driver 24, moves the compression member 22 to open the opening 114 between the compression member 22 and the stationary member 26 of the pretreatment unit 122 to allow receipt of a sample vessel. After a sample vessel is loaded, the driver 24 drives the compression member 22 toward the stationary member 26, resulting in good surface contact between the sample vessel and the compression member and the stationary member and thus improved pretreatment. Once the pretreatment is completed, the driver 24 moves the compression member 22 of the pretreatment unit 122 to further compress the pretreatment segment of the sample vessel to move a selective amount of pretreated sample within the sample vessel to the next processing unit.

The reaction unit 124 can include a plurality of processing stations 150A-150C and is preferably positioned adjacent the pretreatment unit 122. The reaction unit 124 can effect thermal cycling of the sample by selectively moving the sample, with the sample vessel, between the processing stations 150A-150C. The phrase "thermal cycling" as used herein refers to a process of heating and/or cooling a sample in two or more steps, with each step preferably occurring at a different temperature range from the previous step. Each of the processing stations 150A-150C can be maintained at a pre-selected temperature range controlled by a temperature control system 152 and a CPU 174. Although the exemplary embodiment includes three thermal cycling processing stations 150A-150C, the reaction unit 124 can include any number of processing stations 150, depending on the thermal cycling process employed. Alternatively, the reaction unit 124 can incubate a sample at a selective temperature for an isothermal reaction such as for TMA or SDA process.

In PCR based testing, thermal cycling can be used to denature, anneal, elongate and thereby amplify the nucleic acid sample. The PCR thermal cycling steps each occur at specified temperature ranges. Denaturing occurs at approximately 92° C.-96° C.; elongation occurs at approximately 70° C.-76° C.; and annealing occurs at approximately 48° C.-68° C. Each of the PCR thermal cycling steps, i.e. denaturing, annealing, and elongation, can be carried out independently at a separate processing station of the reaction unit 124 by maintaining the processing stations at the temperature ranges effective for carrying out each of the PCR thermal cycling steps. For example, the denaturing step can be carried out at processing station 150A, the elongation step at processing station 150B, and the annealing step at processing station 150C. Alternatively, one or more of the PCR thermal cycling steps can be combined and carried out at the same processing station, thereby reducing the number of processing stations required. For example, denaturing can be carried out at processing station 150A and elongation and annealing can be carried out at processing station 150B, thus, eliminating the need for a third processing station.

Moreover, a processing station can be provided within the reaction unit 122 for cooling of the sample by using a thermal energy element, a Peltier thermal electric element for example, to transfer thermal energy from the processing station. In PCR processing, for example, a processing station can be provided to preserve the nucleic acid sample between process steps by cooling the sample to a refrigeration temperature, e.g., 4° C. Additionally, a processing station can optionally be provided to cool the sample between thermal cycling steps to decrease the temperature down ramping time between successive thermal cycling steps. For example, as denaturing generally occurs at 92° C.-96° C. and annealing generally occurs at a significantly lower temperature, e.g., 48° C.-68° C., the sample can be cooled after denaturing in a cooling processing station, preferably at a temperature lower than the annealing temperature, to bring the sample temperature more quickly into the annealing temperature range. A thermal cycling processing station can optionally include a heat sink 166 coupled to either the compression member 22 or the stationary member 26 to conduct heat away from the station and radiate the heat to the environment.

Each of the illustrated processing stations of the reaction unit 124 includes a compression member 22 and a stationary member 26. The compression member 22 of each thermal cycling processing unit can be coupled to a driver 24 for selectively moving the compression member 22 toward and away from the stationary member 26. As discussed above, the drivers 24 can be any device capable of imparting motion, preferably reciprocal motion, to the compression members. A driver control system 160 is coupled to the drivers 24 to control the operation of the drivers 24. In one preferred embodiment illustrated in FIG. 7, the drivers 24 are electromagnetic actuators coupled to the driver control system 160, which can be, for example, a control system for controlling the reciprocal motion of the actuators. Alternative drivers, compression members and stationary members are described below in connection with FIGS. 8-12. The driver control system 160 is coupled to the CPU 174 such that the sample incubation time period, the pressure and the sample moving speed within the sample vessel can be controlled and coordinated by the CPU 174 to achieve the best reaction results.

Each of the thermal cycling processing station 150A-150C can optionally include an energy transfer element for transferring energy, such as thermal energy, to the sample within the sample vessel. The energy transfer elements can be, for example, an electronic heat element, a microwave generator, a light source, an electronic cooling element, or any another device suitable for applying thermal energy. Each of the energy transfer elements is coupled to the temperature control system 152 to maintain the associated processing station within a selected temperature range. One or more temperature sensors, coupled to the temperature control system 152, can be positioned proximate the processing stations 150A-150C to monitor the temperature of the stations.

Between two adjacent processing units or two adjacent processing stations, at least one layer of energy insulator 146 can optionally be provided to insulate the processing unit or the processing station from adjacent units or stations. An energy insulator layer can also be formed on the boundary of a processing station to prevent energy transfer to or from the environment. The energy insulator 146 can be, for example, an energy shielding layer, an energy absorption layer, an energy refraction layer, or a thermal insulator, depending on the type of energy transfer element employed. A thermal insulator can be constructed from a low thermal conductivity material such as certain ceramics or plastics. In one embodiment, the thermal insulator can be attached to the compression members and the stationary members. Alternatively, the thermal insulators can be separate from the compression members and stationary members and can be controlled independently by a driver to open and close the opening 114. In this embodiment, all the compression members and insulators can open initially to allow loading of the sample vessel, and then, the thermal insulators can compress the sample vessel within the opening to close the vessel and form separate segments within the sample vessel. Additionally, a spring element or other biasing mechanism can be optionally utilized to bias each thermal insulator. Through the spring element, a driver associated with one of the thermal insulators can apply sufficient pressure on the thermal insulator to minimize the quantity of sample remaining in the junction between adjacent processing stations during an incubation period, while still allowing sample flow through the thermal insulator when a higher pressure is applied to the sample in an adjacent processing station. This design simplifies the operation of multiple thermal insulators.

In an alternative embodiment, the processing stations can be spaced apart to inhibit conductive heat transfer between adjacent processing stations and, thereby, eliminate the need for insulators between the stations.

Operation of the thermal cycling reaction unit 124 will be generally described with reference to FIGS. 13A-13G. The thermal cycling process begins by opening each of the processing stations, e.g. first processing station 150A, second processing station 150B, and third processing station 150C, to receive the sample vessel within the opening 114, as illustrated in FIG. 13A. After the sample vessel is loaded with pretreated sample material, or the pretreated sample is dispensed from pretreatment unit 122 into the reaction unit 124, the second processing station 150B and the third processing station 150C are closed by moving the compression member 22B and the compression member 22C of each station toward the respective stationary member 26B and 26C, as illustrated in FIG. 13B. As the second processing station 150B and the third processing station 150C are closed, the sample vessel is compressed between the compression member and the stationary member, displacing the sample within the sample vessel into a segment of the sample vessel adjacent the first processing station 150A.

Next, the compression member 22A and the insulator 146A can compress the sample vessel to adjust the sample volume contained within the segment of the sample vessel adjacent the first processing station 150A, as well as the surface area to volume ratio of the segment. The insulator 146A can then be closed to seal the sample in the first processing station 150A, as illustrated in FIG. 13C. Alternatively, if the device 100 is provided with a sample pretreatment unit, the sample pretreatment unit can function to close the sample vessel within the first processing station 150A. Other alternatives include pre-sealing the sample vessel after loading a sample, or providing the sample vessel with pressure gates, discussed below, formed between adjacent reaction zones. Once the sample is sealed within the first processing station 150A, the sample can be heated or cooled by the first processing station 150A. In PCR thermal cycling, for example, the sample can be heated to a temperature effective to denature the nucleic acid sample. Preferably, the sample vessel is pressed into contact with the compression member 22A and the stationary member 26A by the compression member 22A to flatten the sample vessel and to ensure good thermal contact between the sample vessel and the compression member 22A and the stationary member 26A. The compression member 22A can also optionally periodically squeeze the sample vessel to agitate the sample and to generate sample flow in the segment of the sample vessel during the reaction period to speed up the reaction.

After a predetermined period, the second processing station 150B can be opened to allow the sample to move into the second processing station 150B, as illustrated in FIG. 13D. Next, the first processing station 150A closes, compressing the sample vessel and moving the entire sample, within the vessel 16, into a segment of the sample vessel adjacent the second processing station 150B, as illustrated in FIG. 13E. The third processing station 150C can then open to allow the sample to move into the segment of the sample vessel adjacent the third processing station 150C, as illustrated in FIG. 13F. The second processing station 150B closes, compressing the sample vessel and moving the sample completely into the segment of the sample vessel adjacent the third processing station 150C, as illustrated in FIG. 13G. The sample can then be heated or cooled by the third processing station 150C for a set time period. In PCR thermal cycling for example, the sample can be heated to a temperature effective to anneal the nucleic acid sample in the third processing station 150C. The heat sink 166 can facilitate the temperature transition from the denaturing temperature of the first processing station 150A to the annealing temperature of the third processing station 150C by dissipating excess heat to the environment. Thus, the sample can be moved from the denaturing step at the first processing station to the annealing step at the third processing station.

After a predetermined time period, the second processing station 150B opens to allow the sample to move into the second processing station, as illustrated in FIG. 13F. The third processing station 150C then closes, compressing the sample vessel 16 and moving the sample entirely into the segment of the sample vessel adjacent the second processing station 150B, as illustrated in FIG. 13E. The sample can then be heated or cooled by the second processing station 150B for a set time period. In PCR thermal cycling for example, the sample can be heated to a temperature effective to elongate the nucleic acid sample. Upon conclusion of the elongation step, the sample can be returned to the segment of the sample vessel adjacent the first processing station 150A to repeat the cycle, i.e., denaturing and annealing and elongating or, the sample can be moved to a segment of the sample vessel adjacent the sample detection unit 126 if PCR thermal cycling is completed.

The illustrated thermal cycling reaction unit 124 provides denaturing in the first processing station 150A, annealing in the third processing station 150C, and elongation in the second processing station 150B, as this arrangement is deemed thermodynamically efficient. One skilled in the art will appreciate, however, that the PCR thermal cycling steps can occur in any of the processing stations without departing from the scope of the present invention.

Sample thermal cycling using the reaction unit 124 of the present invention results in faster thermal cycling times and lower energy consumption compared to conventional thermal cycling devices. Sample vessel shape alteration, i.e. flattening, by the reaction unit 124 results in significant increases in the surface/volume ratio and sample vessel contact with the members of the reaction unit. This allows the processing stations of the reaction unit 124 to heat the sample more directly, increasing the sample temperature ramping rate and avoiding unnecessary temperature ramping of the members and thus decreasing the amount of energy consumed. Equally important is that sample vessel shape alteration provides for the uniform transfer of thermal energy to the sample, dramatically reducing reaction mixture temperature gradients. The reaction unit 124 further allows the use of fluid flow to mix the sample as the sample is moved from one processing station to another.

Moreover, the reaction unit 124 allows the use of a disposable, single-use sample vessel that minimizes contamination of the sample, contamination of the reaction unit and exposure of the operator to biohazards. Additionally, the reaction unit 124 does not require a fluid handling system, as the sample can be moved within the sample vessel during processing.

Referring again to FIG. 7, the reaction unit 124 can optionally include a reaction sensor 168 for monitoring the reaction in real-time within the reaction unit 124 by analyzing the sample, including any reaction products from the reaction with the sample. The reaction sensor 168 can include an integral light source 169 for applying excitation energy to the sample within the sample vessel. Alternatively, a light source, or other source of excitation energy, can be provided separate from the reaction sensor 168. The reaction sensor 168 can be an optical sensor for measuring light, for example fluorescent light, emitted from the sample or from fluorescent probes within the sample. In the case of PCR, any known real-time PCR detection system can be employed, including, for example, using fluorescent dyes, such as ethidium bromide, intercalating into the DNA molecule, using a dual labeled probe tagged with a reported dye and a quenching dye, or using hybridization probes, which will result in Fluorescence Resonance Energy Transfer (FRET) only when the two probes are hybridized and in close proximity. In each of these approaches, the fluorescence signal is substantially proportional to the amount of specific DNA product amplified. The reaction detection sensor 168 is placed to monitor the fluorescence from the sample, preferably in the annealing processing station, or other processing stations of the reaction unit, dependent on the assay selected. Multiple sensors or a spectrum sensor can be used when detection of multiple wavelength light is required. The detected signal is then sent to the CPU 174 for further analyzing the amount of product.

Continuing to refer to FIG. 7, the sample detection or analysis unit 126 of the device 100 is provided to analyze the sample after processing by the reaction unit 124. The analysis unit 126 is preferably positioned proximate the reaction unit 124. In one embodiment of the invention, a source of excitation energy, for example a light source, can apply excitation energy to the sample and a signal detector, for example an optical sensor, can detect light emitted from the sample in response to illumination by the excitation light. Specific illustrative practices, include detecting the transmission of light through the sample, detecting reflected light, detecting scattering light, and detecting emitted light. The detected light, in the form of the signal output from the sensor, can be analyzed by a CPU 174 provided in the device through known signal processing algorithms. Suitable sample analysis systems, employing a light source and an optical sensor or sensors, detects signals including light intensity at a given wavelength, phase or spectrum of the light, as well as location of the signal. For example, the flow induced testing system described in U.S. Pat. No. 6,318,191 and the multi-layer testing system described in U.S. Pat. App. Pub. No. US 2004/0105782 A1, both of which are incorporated herein by reference, describe suitable sample analysis systems.

Figure 14:
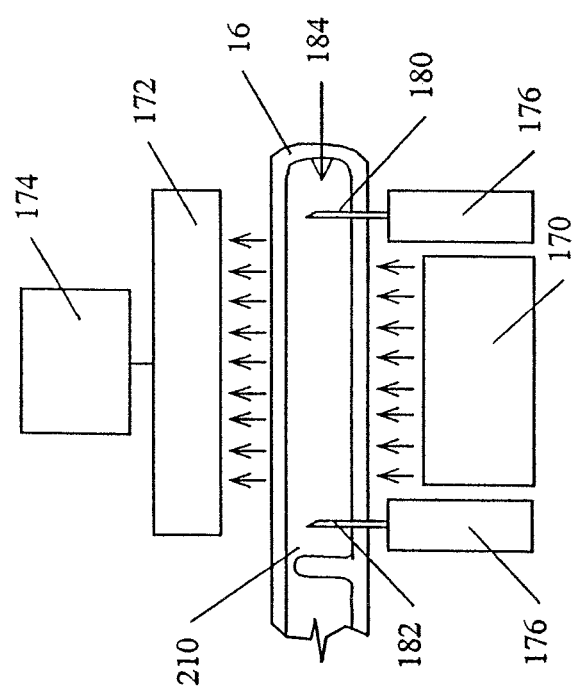
FIG. 14 is a side elevational view, in cross section, of a gel electrophoresis analysis unit of the present invention.

In the case of a PCR based assay, gel electrophoresis or capillary electrophoresis can be employed to analyze the nucleic acid sample, as illustrated in FIGS. 7 and 14. Suitable nucleic acid sizing gels include agarose and polyacrylamide. The gel 184 can be introduced to the sample vessel 16 during processing or, preferably, is pre-loaded into an analysis segment 210 of the sample vessel, as discussed in more detail below. The exemplary analysis unit 126 includes a light source 170 for illuminating the nucleic acid sample and the gel and an optical sensor 172 in the form of linear charge coupled device (CCD). Electrode activators 176 operate to insert a positive electrode 180 and a negative electrode 182 into the sample vessel 16. The positive electrode 180 and the negative electrode 182 are electrically connected to a voltage source, which creates a voltage difference between the electrodes. As nucleic acid products are negatively charged, the nucleic acid products within the sample will move through the gel 184 toward the positive electrode 180. The gel separates the sample components by size, allowing smaller components, such as nucleic acid products, to travel faster, and thus, further, than larger components. A suitable dye or fluorescent tag can be introduced to gel to identify the nucleic acid products. Light from the light source 170 can illuminate the dyed or tagged nucleic acid products in the gel and the optical sensor 172 can then identify the illuminated nucleic acid products. The output signal of the optical sensor 172 can be analyzed by CPU 174 according to known signal processing method to determine the presence, absence, quantity or other condition of the nucleic acid sample.

Alternatively, the nucleic acid sample can be analyzed in accordance with conventional nucleic acid analysis methods, such as, for example, chemiluminescence, fluorescently labeled primers, antibody capture, DNA chip, and/or magnetic bead detection methods.

One skilled in the art will appreciate that the processing units and the processing stations of the above-described exemplary embodiments of the sample processing device of the present invention can be arranged in any order depending on the sample being processed and the process being utilized. The sample processing device of the present invention may include any combination of the processing units and processing stations described herein, as well as additional processing units and processing stations that will be apparent to those skilled in the art upon reading this disclosure. Moreover, the sample processing device may include only a single processing unit, such as, for example, a reaction unit for thermal cycling a sample, or may include a only a single processing station, such as, for example, a processing station for displacing a specified volume of reagent or sample.

FIGS. 8-12 illustrate alternative embodiments of a reaction unit 250 for thermal cycling a sample according to the present invention. The reaction unit 250 can include one or more openings 252 for receiving one or more sample vessels 16. The embodiments illustrated in FIGS. 8-12 have three openings 252, permitting the simultaneous thermal cycling of up to three samples. The reaction unit 250 comprises three processing stations: a first processing station 254, a second processing station 256, and a third processing station 258. Thermal insulators 260A-260D are positioned between the processing stations and at the top of the first processing station 254 and the bottom of the third processing station 258.

Figure 8:
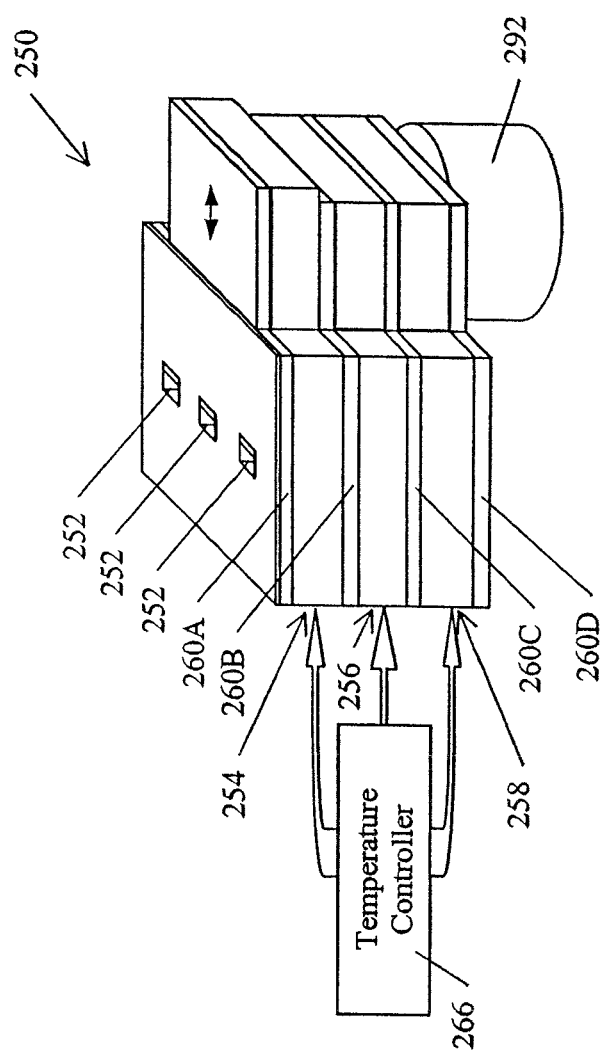
FIG. 8 is a perspective view of an embodiment of a thermal cycling processing unit according to the present invention.
Figure 10:
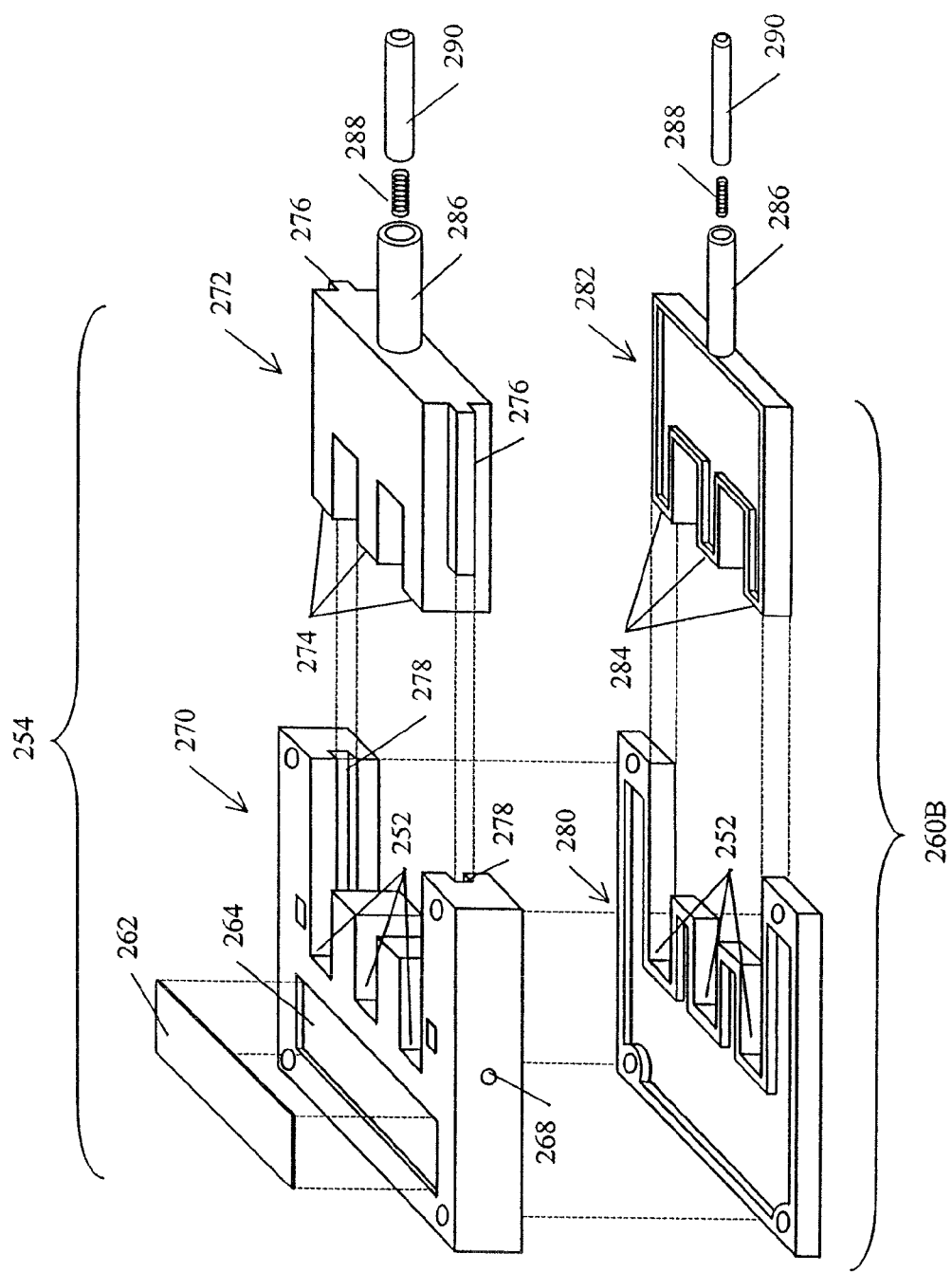
FIG. 10 is a partially exploded, perspective view of a processing station of the processing unit of FIG. 8, illustrating a heat block unit and an insulator block unit of the processing station.

Referring specifically to FIGS. 8 and 10, the first processing station 254, as well as the second and third processing stations 256 and 258, includes an embedded heat element 262 for transferring thermal energy to the sample vessel when the sample vessel is positioned within an opening 252. The heat element 262 can be a Kapton heater, a Nomex heater, a Mica heater, a silicone rubber heater or any other thermal energy transfer element suitable for delivering thermal energy. The heat element 262 can be seated in a recess 264 formed in the processing station 254 and secured to the processing station by an adhesive or other attachment means. The heat element 262 of each of the processing stations is preferably coupled to a temperature controller 266 for controlling the temperature of the heat element. One or more temperature sensors 268 can be positioned in the processing station 254 to measure the temperature of the processing station 254. The temperature sensor 268 can be coupled to the thermal controller 266 such that the temperature controller 266 can monitor and adjust the temperature of the processing station in a feedback control manner.

Figure 11:
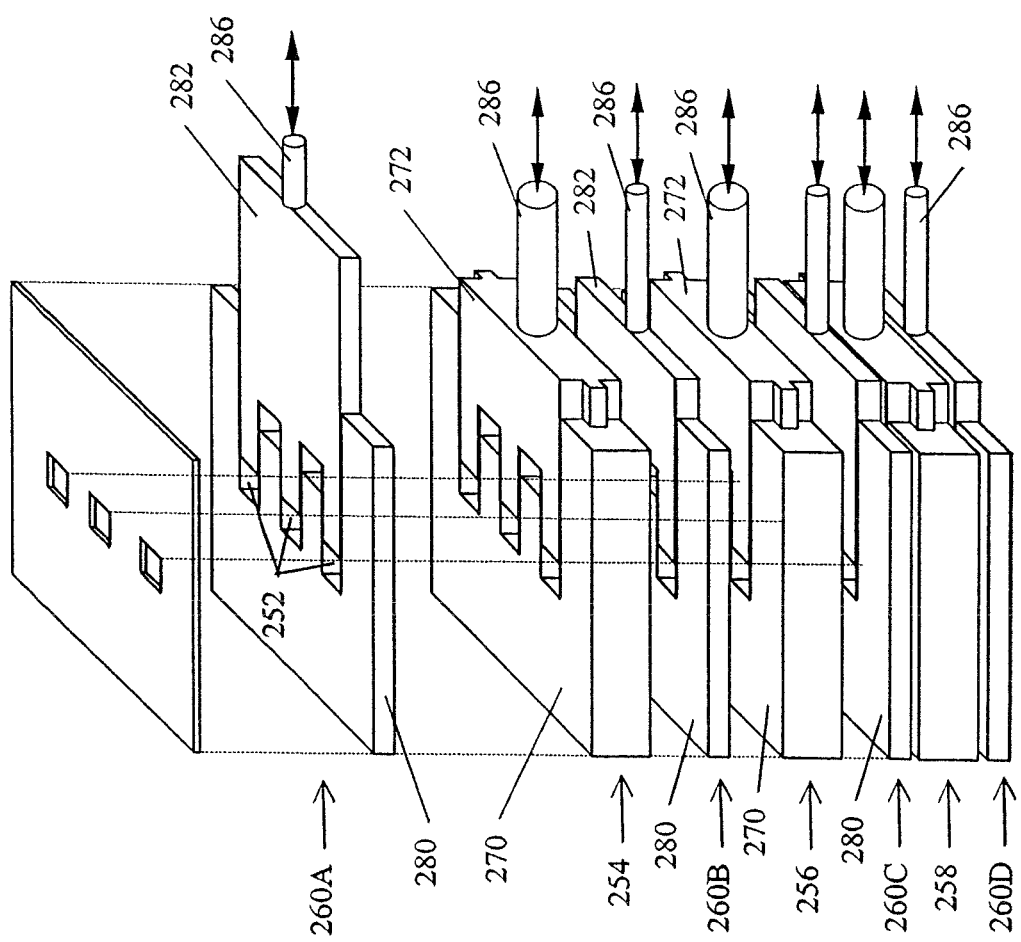
FIG. 11 is a partially exploded, perspective view of the processing unit of FIG. 8, illustrating a plurality of heating block units and insulator block units.
Figure 12:
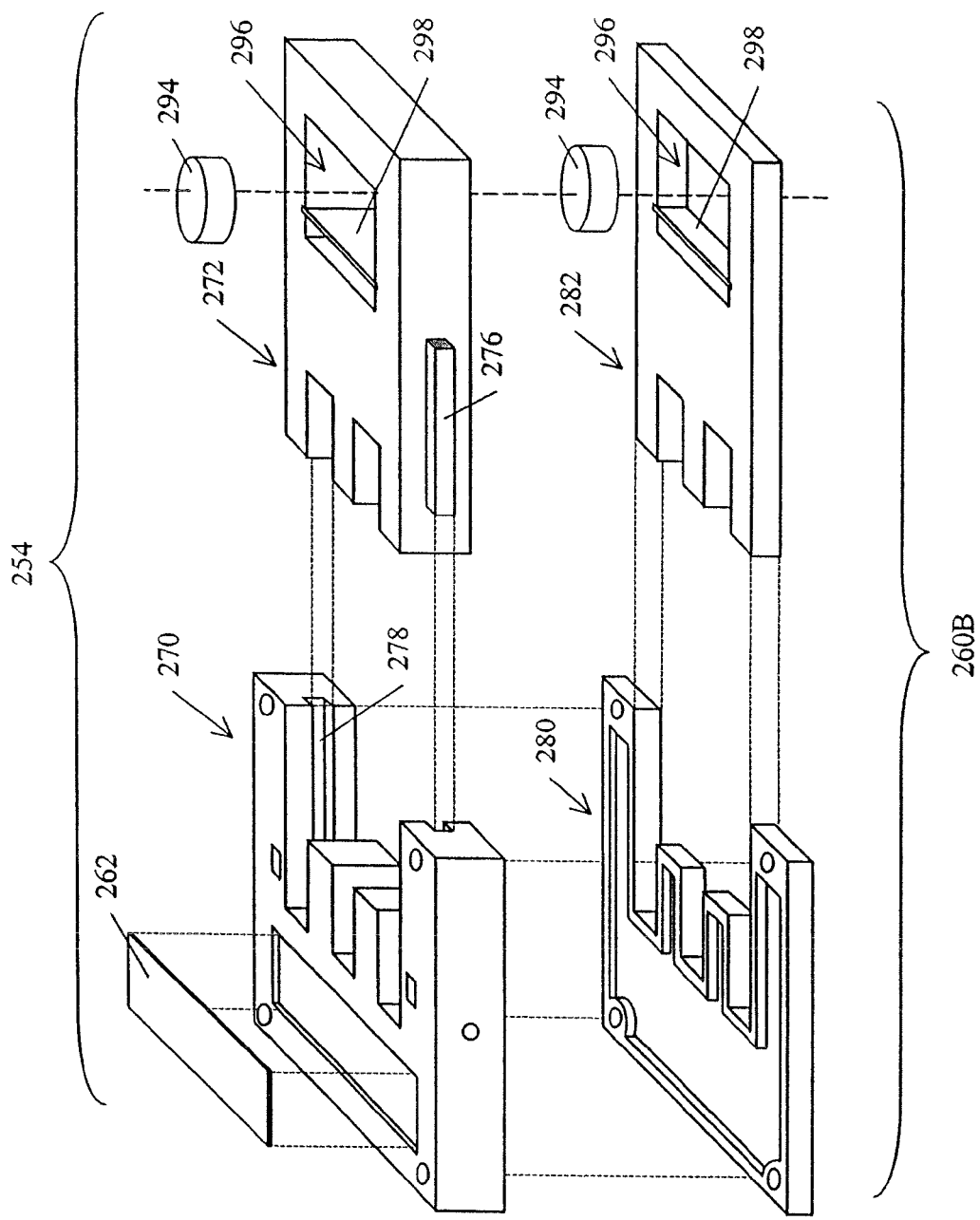
FIG. 12 is a partially exploded, perspective view of a processing station of an alternative embodiment of a processing unit according to the present invention.

Referring to FIGS. 10 and 11, each processing station comprises a stationary member 270 and a compression member 272 adapted to compress the sample vessel selectively within one or more of the openings 252 and thereby move the sample within the sample vessel. The compression member 272 is preferably complimentary in shape to the stationary member 270 and includes a plurality of finger-like closure elements or shutters 274 sized and shaped to slide within the openings 252. Guide rails 276 are positioned on either side of the compression member. The guide rails 276 are preferably sized and shaped to fit within grooves 278 formed in the side walls of the stationary member 270. The combination of the guide rails 276 and the grooves 280 allow the compression member 272 to reciprocate relative to the stationary member 270 to selectively open and close the openings 252.

Each thermal insulator 260 can be configured in a manner analogous to the processing stations. For example, the thermal insulator 260B comprises an insulator stationary member 280 and an insulator compression member 282 adapted to compress a sample vessel within one or more of the openings 252. The insulator compression member 282 includes a plurality of finger-like closure elements or shutters 284 sized and shape to slide within the openings 252 to selectively open and close the openings 252.

Figure 9:
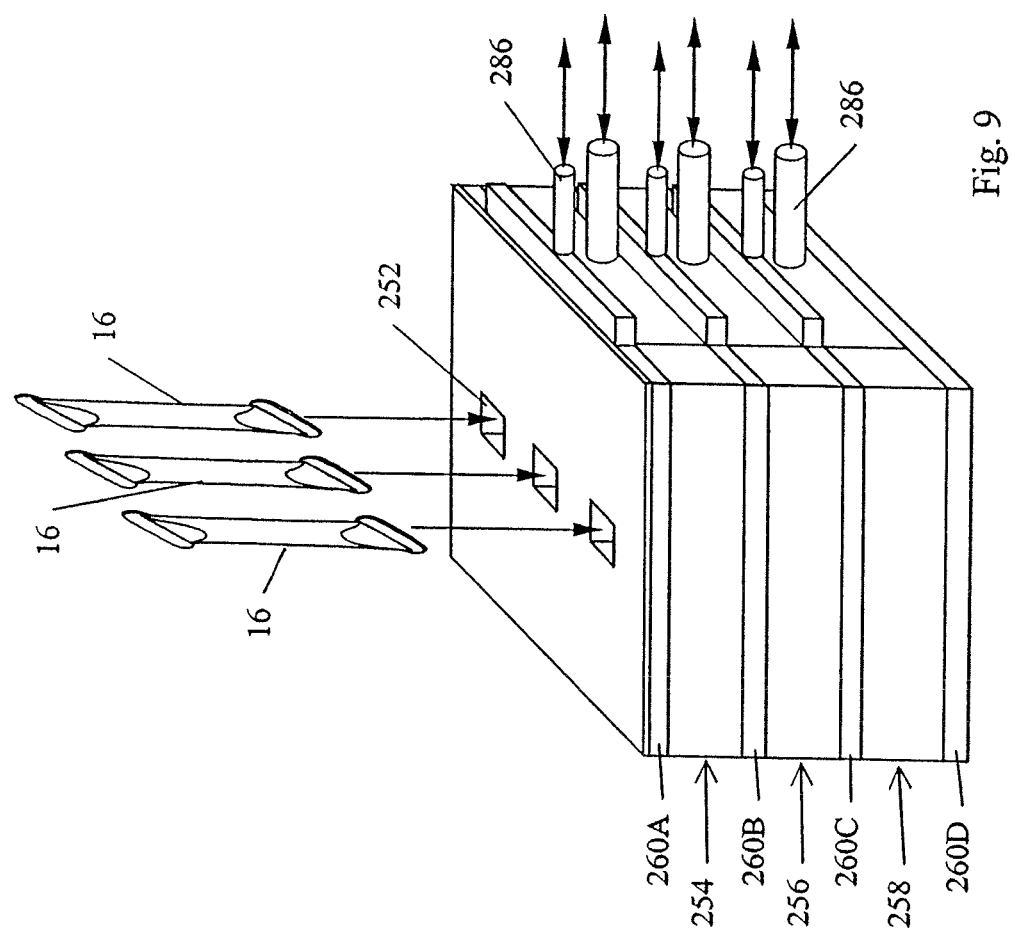
FIG. 9 is a perspective view of the processing unit of FIG. 8.

Each compression member 272 and insulator compression member 282 is coupled to a driver, such as an electromagnetic driver mechanism, as described above, or any other mechanism for imparting motion, preferably reciprocating motion, to the compression members. Each compression member can be coupled to an arm 286 for providing a connection between the compression member and the driver, as best illustrated in FIGS. 9-11. In one embodiment, illustrated in FIG. 10, the arms 286 are hollow tubes that receive coiled springs 288 and dowels 290. The springs 288 operate to bias the compression members 272, 282 in a direction away from the stationary member 270 and the insulator stationary member 280, respectively. An elastic element, such as the coiled spring used here, provides a simple mechanism for assisting the driver to regulate the compressing pressure applied to the sample vessel. The driver can be a motor 292 for driving a rotating shaft, as best illustrated in FIG. 8. The rotary motion of the shaft can be translated to reciprocating motion through cams 294 provided for each of the compression members 272 and 282. The cams 294 are coupled to the arms 286. The cams 294 can be configured to selectively open and close the compression members 272 and 282 in accordance with conventional cam design methods.

In one alternative embodiment of the reaction unit, the compression members 272 and 282 of each of the processing stations and insulators include holes 296 for receiving a cam 294 and a linear spring element 298. Spring elements 298 each operate to bias a respective compression member in a direction away from the corresponding stationary member. The cams 294, in combination with the springs 298, act to impart reciprocating motion to the actuators and regulate the compressing pressure on the sample vessel.

Figures 19A, 19B, 19C:
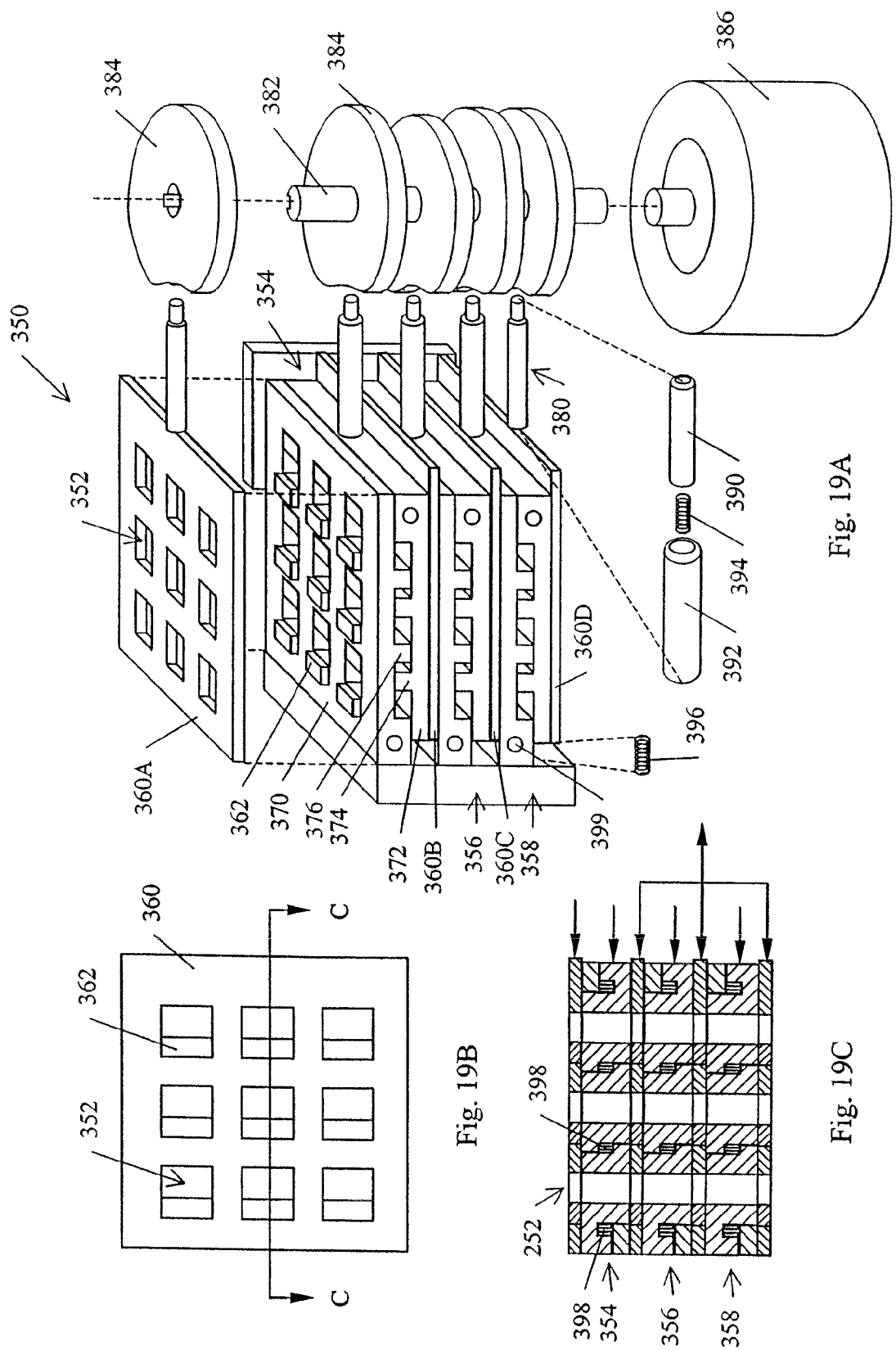
FIGS. 19A-19C illustrate an alternative embodiment of a processing unit of the present invention.

FIGS. 19A-19C illustrate a further embodiment of the reaction unit of the present invention. The reaction unit 350 includes nine openings 352 for receiving up to nine sample vessels simultaneously. The reaction unit 350 includes three processing stations: a first processing station 354, a second processing station 356, and a third processing station 358. Thermal insulators 360A-360D are positioned adjacent each of the processing stations and at the top of the first processing station 354 and the bottom of the third processing station. Top thermal insulator 360A and bottom thermal insulator 360D are movable independent of the first processing station 354 and the third processing station 358, respectively. Intermediate thermal insulators 360B and 360C are coupled to the first processing station 354 and the second processing station 356, respectively.

Each processing station comprises a stationary member 370 and a complementary compression member 372 adapted to compress the sample vessel selectively within one or more of the openings 352 and thereby move the sample within the sample vessel. Each stationary member 370 has a projection 374 aligned with one of the openings 352. The compression members 372 are each provided with a projection 376, positioned on an opposite side of the opening 352. When a compression member 372 is slid on the corresponding stationary member 370, the projections 374 and 376 engage and close the openings 352 therebetween.

Each compression member 372, as well as intermediate thermal insulators 360B and 360C, include an arm 380 coupled by a cam 384 to a rotary shaft 382. A stationary insulator member 362 is coupled, and aligned with an edge of each opening 352 on each stationary member 370. Each stationary insulator member 362 is inserted in each of the openings of a movable insulator compression member 360 to react to compression and open or close the opening. The shaft 382 is rotated by a stepper motor or a servo motor 386. The cams 384 translate the rotation of the shaft 382 into linear reciprocal motion, which is imparted to the arms 380 to effect selective opening and closing of the openings 352 and compression of the sample vessels therein.

Each arm 380 includes an inner shaft 390 received within an outer sleeve 392. A spring 394 is interposed between the inner shaft 390 and the respective compression member or thermal insulator. A second spring 396 is positioned on an opposite side of the respective compression member or thermal insulator. The spring 394 cooperates with the second spring 396 to allow the compression member or thermal insulator to "float" along the axis of the arm 380. In this manner, the arm 380 can apply sufficient force to the compression member or thermal insulator to compress the sample vessel within an opening 352 and, thereby, displace substantially all of the sample from the compressed portion of the sample vessel. An increase of pressure within the sample vessel, for example, from the compression of an adjacent portion of the sample vessel, however, can cause the sample to displace within the sample vessel through the compressed portion of the sample vessel, as the springs 394 and 396 will allow small axial movements of the compression member or thermal insulator.

Each stationary member 370 and compression member 372 can be provided with an embedded thermal energy transfer device 398 for each opening 352 to apply thermal energy to the sample vessel within the opening 352. In addition, the stationary member 370 and compression member 372 can include temperature sensors 399 associated with each energy transfer device 398 to monitor the temperature of the sample vessel.

FIGS. 15A and 15B illustrate embodiments of a sample vessel 16 according to the present invention. The illustrated sample vessel 16 is a closed tubule system that provides a disposable, single use container and reaction vessel for the sample. The sample vessel 16 can be constructed of a resiliently compressible, flexible, and ultra-high strength material, such as polyethylene or polyurethane. The sample vessel 16 can have a seamless, flattenable cross-sectional profile and thin-walled construction that is optimized for fast and uniform heat transfer, for maximum surface contact with the sample, and for high pressure resistance. Preferably, the walls are constructed to converge when the sample vessel is compressed in a direction perpendicular to the longitudinal axis of the sample vessel such that the volume of the compressed portion of the sample vessel decreases and the ratio of the surface area to the volume of the compressed portion increases, without fracturing of the sample vessel. In one illustrative preferred practice, the walls of the sample vessel 16 have a wall thickness of approximately 0.01 mm to 0.5 mm. Experimental results indicate that constructing a sample vessel having a wall thickness within this preferred range significantly increases the efficiency of heat transfer to the sample. In an alternative embodiment, a two-layer wall structure can be used, with the inner layer providing biocompatibility, using material such as polyethylene or polyurethane, and the outer layer providing lower permeability, using material such as high density polyethylene or aluminum foil. In addition, the material selected to construct the portions of the wall of the sample vessel, such as a detection segment of the sample vessel 16, can be optically transmissive over a selected wavelength range to facilitate optical analysis of the sample within the sample vessel.

The sample vessel 16 can be divided into multiple segments by one or more pressure gates 32. In the case of PCR testing, for example, the sample vessel can be divided into a sample collection segment 205, a sample pretreatment segment 206, a sample reaction segment 208, and a sample analysis segment 210. The illustrated pressure gates 32 are internal to the tubule structure of the vessel 16 and provide a fluid tight seal between the segments of the sample vessel 16, under normal operating conditions. The pressure gates are formed by placing the sample vessel between sealing heads, squeezing the sealing heads together under pressure to compress the sample vessel, and applying energy across the compressed vessel to create a seal. For example, RF energy or direct heat may be applied to create a heat seal. Thus, the pressure gates are formed by a bonding of opposing wall portions of the vessel to one another. As shown in FIGS. 15A-B, the resulting adjacent segments are separated from one another by only a pressure gate, and opposing wall portions of the vessel are not bonded to one another except at pressure gates. When the sealing heads extend beyond the edges of the sample vessel, the pressure gate, when formed, extends across the entire width of the vessel. Preferably, the pressure gates 32 open upon the application of pressure greater than a certain value, for example, approximately 2 or 3 atmospheres. When external pressure is provided to one segment, the pressure gate 32 can open, allowing the sample to flow from the high pressure compartment to the low pressure compartment.

The sample vessel 16 can include a handling portion having a generally rigid construction to facilitate handling of the sample vessel. The handling portion can be coupled to one or more of the segments of the sample vessels used to contain the sample. For example, the handling portion can be a cylindrical sleeve constructed of a generally rigid material, such as a plastic or a metal, that is sized and shaped to fit over one or more of the segment of the sample vessel. In one embodiment, the cylindrical sleeve can be removable and replaceable. Alternatively, the handling portion can be a rigid segment, such as a rigid ring, positioned at an end of the sample vessel or between two segments of the sample vessel. In the embodiments illustrated FIGS. 15A and 15B, the handling portion is a segment of the sample vessel having an increased wall thickness. For example, the sample collection segment 205 and the sample pretreatment segment 206 have a wall thickness greater than the wall thickness of the reaction segment 208. The increased wall thickness provides sufficient rigidity to the sample collection segment 205 and the sample pretreatment segment 206 to facilitate handling of the sample vessel 16. In one embodiment, the wall thickness of the handling portion is greater than 0.3 mm.

The sample vessel 16 can include an instrument, such as a sampling pipette or a needle 107, for direct collection of the sample to be treated and analyzed within the sample vessel 16, as illustrated in FIG. 15A. The needle 207 can be positioned at one end of the sample vessel 16 and can be connected to the sample collection chamber 205 through a conduit 209 formed in the wall of the sample vessel 16. A needle cover 211 can be provided to secure the needle 207 prior to and after use. The needle cover 211 can be, for example, a penetrable rubber cover or a removable plastic cover.

In another embodiment, illustrated in FIG. 15B, a sampling instrument 214, such as a pipette, a stick, or a tweezer, can be coupled to a cover 212 that selectively closes the conduit or opening 209 formed in the wall of the sample vessel. The cover 212 can include a reservoir 216 for containing a reagent and a sample during sampling. For sampling, the cover 212 can be removed from the sample vessel to expose the sampling instrument 214. The sampling instrument 214 can be used to collect the sample, by pipetting, swabbing, or gathering the sample, for example, and then the sampling instrument 214 can be inserted into the sample collection segment 205 through the conduit 209. The sample can then be introduced to the sample collection segment 205 by compressing the cover 216 to displace the sample from the reservoir 216. Alternatively, the sample can be introduced to the sample collection segment 205 or to another segment of the sample vessel, depending of the segments present in the sample vessel, after collection by a separate instrument.

Sample vessel 16 can be particularly suited for PCR testing using the sample processing device of the present invention, as described above. For example, nucleic acid extraction can be performed within the sample pretreatment segment 206 of such a sample vessel 16. A cell lyses reagent, for example, GENERELEASER® from Bioventures, Release-ITT™ from CPG Biotech, or Lyse-N-Go™ from Pierce, or other extraction reagents can be introduced to the pretreatment segment 206 to extract nucleic acid from the initial sample. Extraction reagents can be stored within the pretreatment segment 206 or can be delivered to the segment. Additionally, one or more filters can be positioned within the pretreatment segment 206 of the sample vessel to separate nucleic acid from unwanted cellular debris.

After incubation of the sample for certain time period, a portion of pretreated sample can be moved into the reaction segment 208. For a reaction sample volume of approximately 5 μl-25 μl, a PCR reaction segment 208 of the sample vessel 16 according to one illustrative practice of the invention has a wall thickness, indicated by reference character t in FIG. 15A, of approximately 0.01 mm-0.3 mm, a diameter of less than approximately 6 mm, and a length of less than approximately 30 mm. PCR reagents, such as nucleotides, oligonucleotides, primers and enzymes, can be pre-packaged in the reaction segment or reaction segments 206, or can be delivered, for example, through the walls of the sample vessel using a needle, using for example, a reagent injector cartridge described below, before moving the sample into the segment.

A pre-packaged reagent storage segment 214 can be used to stored a pre-packaged reagent. Such a reagent storage segment can be formed between any two adjacent processing segments and may store any reagent needed for a reaction. For example, the reagent storage section 214 can store PCR reagents, while reagent storage sections 236 and 244, described below, may include detection reagents. If the reagent storage segment 214 is utilized, the sample vessel 16 can be compressed at the reagent storage segment 214 to displace the reagent into the pretreatment segment 206. Alternatively, the sample can be moved from the pretreatment segment 206, through the reagent storage segment 214 where mixing with the reagent, to the reaction segment 208.

Figure 16:
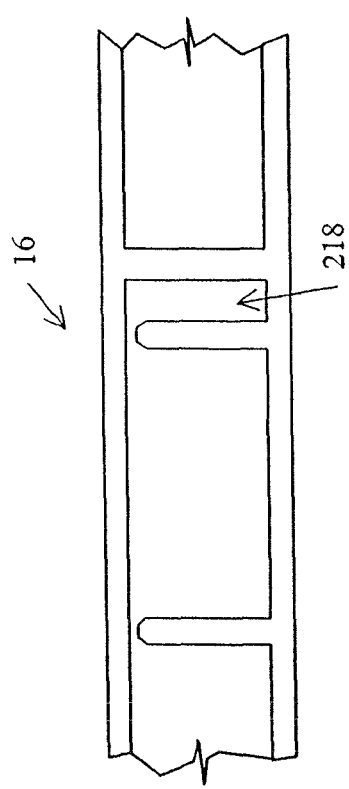
FIG. 16 is a side elevation view, in cross section, of a portion of a sample vessel according to the present invention, illustrating an injection channel formed in the sample vessel.
Figure 17:
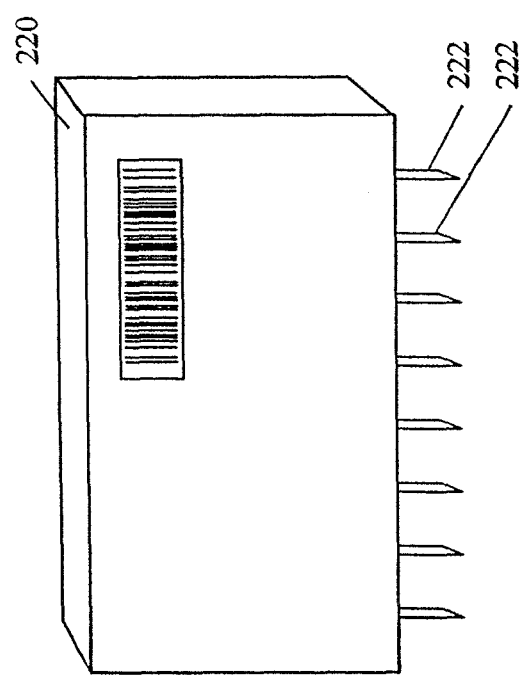
FIG. 17 is a side elevational view of a reagent cartridge according to the present invention.

A self-sealing injection channel 218 can be formed in the sample vessel to facilitate delivery of reagent or other materials to the sample vessel, as illustrated in FIG. 16. The illustrated self sealing injection channel 218 is normally substantially free of fluidic material and is capable of fluid communication with the adjacent segment in the vessel. An injection of reagent through an injection channel occurs preferably prior to moving any sample into the segment to avoid contamination. In addition, the sample treatment devices of the invention can utilize a reaction cartridge 220 with a single or multiple needles 222 in fluid communication with one or more reservoirs, as illustrated in FIG. 17. The reaction cartridge 220 can be used to inject or deposit reagent or other materials, simultaneously, or sequentially into multiple segments of the sample vessel. Suitable self-sealing injection channels and reagent cartridges are described in U.S. Pat. No. 6,318,191, incorporated herein by reference.

One skilled in the art will appreciate that while it may be preferable for the wall of the sample vessel to uniform along the circumference and the longitudinal axis of the vessel, only a portion of the wall along the circumference and/or the longitudinal axis of the vessel need be resilient and compressible and have the preferred thickness to effect flattening of the sample vessel. Thus, the sample vessel need not have a uniform axial or circumferential cross-section.

PCR thermal cycling can be performed in the reaction segment 208 of the sample vessel 16. The thin walled, compressible construction of the sample vessel 16 greatly improves the rate and efficiency of thermal cycling. The construction of the sample vessel allows the vessel to deform or flatten readily, increasing thermal contact with the reaction unit of the device 10 and increasing surface/volume ratio of the sample within the sample vessel. As a result, the reaction mixture ramping rate is increased and thermal energy is more uniformly transferred to the sample.

PCR analysis can be performed in the sample vessel 16. For example, real-time detection methods can be used within the reaction segment 208; gel electrophoresis or other nucleic acid detection methods can be used within the analysis segment 210 to analyze the sample. In the case of gel electrophoresis, a gel can be introduced to the analysis segment 210 to facilitate gel electrophoresis, as described above in connection with FIG. 14.

In one preferred embodiment, illustrated in FIG. 15A, the analysis segment 210 is divided into two electrophoresis capillaries, namely, a sample capillary 230 and a control capillary 232, by a diametrically-central divider 234. Pressure gates 32 at either end of the capillaries control the movement of the sample and the reagents into both capillaries. Each capillary is filled with an electrophoresis gel such that gel electrophoresis can be performed simultaneously in both capillaries. A pair of electrodes 240, for both capillary 230 and 232, can be positioned within the walls of the sample vessel. A reagent storage segment 236 can be provided at the proximal end of the sample capillary 230 for storing reagent within the sample vessel prior to the sample entering the sample capillary 230. A control material can be stored in a control storage segment 242 positioned at the proximal end of the control capillary 232. A reagent can be stored in a reagent segment 244 positioned at the distal end of the capillaries and in communication with both the sample capillary 230 and the control capillary 232 for detection or display signal. The presence of the control capillary 232 facilitates detection and analysis of the sample by providing a basis of comparison for the sample analysis.

One skilled in the art will appreciate that the number of segments within the sample vessel is dependent upon the sample being processed and the processing methods being employed. For example, in the case of PCR testing, the number of segments within the sample vessel can be three or more. Alternatively, thermal cycling and analysis may be performed in one segment, reducing the number of segments to two. In certain cases, an isothermal nucleic acid amplification method, for example, only one segment may be necessary.

FIG. 18 illustrates a sample vessel 416 particularly suited for use in a multi-opening sample processing device such as, for example, the sample processing device illustrated in FIG. 6. The sample vessel 416 includes an opening 420 for receiving the sample, a cap or closure 424 for selectively closing and sealing the opening 420, and a sample containing portion 426 within which the sample can be treated. The opening 420 is formed in a handling portion 428 that is preferably constructed of a generally rigid or semi-rigid material, such as plastic or metal, to facilitate handling of the sample vessel 416. The handling portion 428 includes a collar 430 against which the cap 424 seats. Sample material can be introduced into the sample containing portion 426 of the sample vessel 416 through the opening 420. The collar 428 preferably tapers from a larger diameter to the smaller diameter of the sample containing portion 426. The sample containing portion 426 is preferably constructed of a resiliently compressible, flexible, and ultra-high strength material, such as polyethylene or polyurethane. The sample containing portion 426 can have a seamless, flattenable cross-section profile and thin-walled construction that is optimized for fast and uniform heat transfer, for maximum surface contact with the sample, and for high pressure resistance. In accordance with one embodiment, the sample containing portion 426 has a wall thickness of approximately 0.01 mm-0.3 mm. Preferably, the sample containing portion 426 of the sample vessel 416 is in a flattened state prior to introduction of the sample. Introduction of the sample to the sample containing portion 426 will cause the walls of the sample containing portion to separate and the volume of the sample containing portion to increase. Compression of a selected portion of the sample containing portion 426 can cause the sample to displace to another portion within the sample containing portion along the length of the sample vessel. The surface of the sample vessel can be chemically treated to reduce a surface effect on the reaction.

The embodiments of the sample vessel described herein in connection with FIGS. 14-16 and 18, are not limited to use with the embodiments of the sample processing device described herein. The sample vessel of the present invention may be used with any sample testing or processing system Likewise, the sample processing device of the present invention is not limited to use with the sample vessels described herein. Other sample vessels may be used without departing from the scope of the present invention.

Certain changes may be made in the above constructions without departing from the scope of the invention. It is intended that all matter contained in the above description or shown in the accompanying drawings be interpreted as illustrative and not in a limiting sense.

It is also to be understood that the following claims are to cover all generic and specific features of the invention described herein, and all statements of the scope of the invention which, as a matter of language, might be said to fall therebetween.

Having described the invention, what is claimed as new and desired to be secured by Letters Patent is:

1. A sample processing apparatus, comprising:
   (a) a sample-containing vessel comprising:
      an opening to receive at least one sample;
      a tubule which comprises opposing walls constructed of a flexible material permitting substantial flattening of a selected section of the sample-containing portion;
      at least 3 segments within the tubule, the at least 3 segments comprising: a first segment adjacent to the opening and capable of accepting a sample; a second segment adjacent to the first segment and distal to the opening, and containing a nucleic acid extraction agent; and a third segment adjacent to the second segment and distal to the first segment, and containing a PCR reagent; wherein each segment is fluidically isolated at least in part from an adjacent segment by a pressure gate comprising portions of the opposing walls directly bonded to one another, and wherein the pressure gate is opened by application of fluid pressure on a segment that is fluidically isolated in part by the pressure gate and each segment is so thermally conductive as to permit the transfer of thermal energy to and from the contents of each segment, so compressible as to permit opposing wall portions of each segment to touch one another when each segment is compressed, and so expandable as to receive a volume of fluid expelled from another segment when not so compressed; and
      a cover for closing the opening; and
   (b) a thermal cycling unit capable of amplifying extracted nucleic acid, the thermal cycling unit having at least a first processing station and a second processing station, each processing station defining a temperature zone, wherein thermal cycling is performed by alternatively transferring the contents of the sample vessel between the at least two processing stations.

2. The sample processing apparatus of claim 1, wherein the vessel has a filter contained therein structured to separate selected components of a sample material from other components of the sample material.

3. The sample processing apparatus of claim 1, wherein the nucleic acid extraction reagent is a cell lysis reagent.

4. The sample processing apparatus of claim 1, wherein the PCR reagent comprises at least one nucleotide, an enzyme, a DNA polymerase, a template DNA, an oligonucleotide, a primer, a dye, a marker, a molecular probe, a buffer, and a detection material.

5. The sample processing apparatus of claim 1, wherein the vessel contains a micro-array bio-chip for analyzing the sample.

6. The sample processing apparatus of claim 1, further comprising:
   an opening to receive at least one sample containing vessel; and
   a detection unit capable of detecting a signal from amplified nucleic acid.

7. The sample processing apparatus of claim 1, wherein the vessel includes a self-sealing injection channel formed therein, the self-sealing injection channel being capable of fluid communication with the sample material in the sample-containing vessel.

8. The sample processing apparatus of claim 1, wherein the walls comprise at least two layers.

9. The sample processing apparatus of claim 8, wherein the walls comprise a first layer having a first permeability; and a second layer exterior to the first layer and having a second permeability lesser than the first permeability.

10. The sample processing apparatus of claim 9, wherein the first layer is constructed of biocompatible material.

11. The sample processing apparatus of claim 1, wherein at least a portion of the walls are optically transmissive over a selected wavelength range.

12. The sample processing apparatus of claim 1, wherein the cover comprises a reservoir.

13. The sample processing apparatus of claim 1, further comprising a sampling instrument attached to the cover.

14. The sample processing apparatus of claim 13, wherein the sampling instrument is selected from one of a pipette, a needle, a stick, and a tweezer.

15. The sample processing apparatus of claim 1, wherein the segments form a substantially linear array.

16. The sample processing apparatus of claim 1, wherein the segments form a contiguous array.

17. The sample processing apparatus of claim 1, wherein said sample containing vessel further comprises a fourth segment adjacent to the third segment and distal to the second segment, wherein the fourth segment contains a PCR reagent.

18. The sample processing apparatus of claim 1, wherein at least one pressure gate extends substantially across the entire width of sample-containing vessel.

19. The sample processing apparatus of claim 1, wherein said sample containing vessel further comprises a handling portion coupled to the sample containing vessel, the handling portion having a generally rigid construction to facilitate handling of the sample processing apparatus.

* * * * *